US012667834B2

(12) United States Patent
Helal et al.

(10) Patent No.: US 12,667,834 B2
(45) Date of Patent: Jun. 30, 2026

(54) BIMETALLIC NANOALLOY COMPOSITE

(71) Applicant: KING FAHD UNIVERSITY OF PETROLEUM AND MINERALS, Dhahran (SA)

(72) Inventors: Aasif Helal, Dhahran (SA); Mohammed Ahmed Sanhoob, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 489 days.

(21) Appl. No.: 18/328,400

(22) Filed: Jun. 2, 2023

(65) Prior Publication Data

US 2024/0399344 A1 Dec. 5, 2024

(51) Int. Cl.

| | |
|---|---|
| ***B01J 23/89*** | (2006.01) |
| ***B01J 21/18*** | (2006.01) |
| ***B01J 23/75*** | (2006.01) |
| ***B01J 23/755*** | (2006.01) |
| ***B01J 23/78*** | (2006.01) |
| ***B01J 35/23*** | (2024.01) |
| ***B01J 35/30*** | (2024.01) |
| ***B01J 35/61*** | (2024.01) |
| ***B01J 37/02*** | (2006.01) |
| ***B01J 37/03*** | (2006.01) |
| ***B01J 37/04*** | (2006.01) |
| ***B01J 37/08*** | (2006.01) |
| ***B01J 37/16*** | (2006.01) |
| ***C07C 1/12*** | (2006.01) |
| ***C07D 235/08*** | (2006.01) |

(52) U.S. Cl.

CPC ............ *B01J 35/393* (2024.01); *B01J 21/18* (2013.01); *B01J 23/75* (2013.01); *B01J 23/755* (2013.01); *B01J 35/23* (2024.01); *B01J 35/394* (2024.01); *B01J 35/615* (2024.01); *B01J 37/0236* (2013.01); *B01J 37/031* (2013.01); *B01J 37/04* (2013.01); *B01J 37/08* (2013.01); *B01J 37/086* (2013.01); *B01J 37/16* (2013.01); *C07C 1/12* (2013.01); *C07D 235/08* (2013.01); *C07C 2523/75* (2013.01); *C07C 2523/755* (2013.01)

(58) Field of Classification Search

CPC ........ B01J 35/393; B01J 35/394; B01J 35/23; B01J 35/615; B01J 23/89; B01J 23/78

See application file for complete search history.

(56) References Cited

U.S. PATENT DOCUMENTS 11,406,971 B2 8/2022 Luz Minguez et al.

FOREIGN PATENT DOCUMENTS

| | | |
|---|---|---|
| CN | 104356170 B | 2/2017 |
| CN | 105837512 B | 4/2018 |
| CN | 108772103 A | 11/2018 |
| CN | 106391029 B | 12/2018 |
| CN | 110893347 A | 3/2020 |

OTHER PUBLICATIONS

Marzieh Janani, et al., "An Efficient Synthesis of Benzimidazole and Benzothiazole Derivatives Using a Nickel(II) Metal-Organic Framework", Current Organic Synthesis, vol. 17, No. 2, Mar. 1, 2020, pp. 109-116 (Abstract only).

Timothy Zurrer, et al., "Bimetallic RuNi-decorated Mg-CUK-1 for oxygen-tolerant carbon dioxide capture and conversion to methane", Nanoscale, vol. 14, Issue 42, Oct. 13, 2022, pp. 15669-15678.

*Primary Examiner* — Bruck Kifle

(74) *Attorney, Agent, or Firm* — Oblon, McClelland, Maier & Neustadt, L.L.P.

(57) ABSTRACT

A method of making a bimetallic nanoalloy composite includes mixing and dissolving a nickel salt, a cobalt salt, and an aromatic carboxylic acid in a first solvent to form a first mixture; mixing acetic acid with the first mixture and heating at a temperature of 150 to 200 degrees Celsius (° C.) form a second mixture; washing the second mixture with at least one organic solvent and drying to form a bimetallic metal-organic framework (CoNiBTC); heating the CoNiBTC at a temperature of 600 to 900° C. under a nitrogen stream to form a pyrolyzed composite; and cooling the pyrolyzed composite and exposing to a gas mixture to form the bimetallic nanoalloy composite. A method of making a benzimidazole compound. A method of making methane from $CO_2$.

12 Claims, 32 Drawing Sheets

BIMETALLIC NANOALLOY COMPOSITE

STATEMENT REGARDING PRIOR DISCLOSURE BY THE INVENTORS

Aspects of this technology are described in "Bimetallic metal-organic framework derived nanocatalyst for $CO_2$ fixation through benzimidazole formation and methanation of $CO_2$" published in Catalysts, Volume 13, Issue 2, 357, which is incorporated herein by reference in its entirety.

STATEMENT OF ACKNOWLEDGEMENT

This research was supported by the King Fahd University of Petroleum and Minerals (KFUPM) under the grant ORCP2390.

TECHNICAL FIELD

The present disclosure is directed to a bimetallic nanoalloy composite, particularly to a method of making the bimetallic nanoalloy composite (CoNiBTC).

DESCRIPTION OF THE RELATED PRIOR ART

The description of the related prior art provided herein is for the purpose of generally presenting the context of the disclosure. Work of the presently named inventors, to the extent described in this background section, as well as aspects of the description which may not otherwise qualify as prior art at the time of filing, are neither expressly nor impliedly admitted as prior art against the present invention.

Rapid industrial and technological advancements, especially over the last century, have impacted the environment in many ways. To name a few: air and water pollution, depletion of natural resources, and waste management constitute some of the significant challenges to deal with. Certain industrial processes and land-use changes also emit carbon dioxide ($CO_2$). Gases that trap heat in the atmosphere are called greenhouse gases. $CO_2$ is the primary greenhouse gas emitted through human activities. The main human activity that emits $CO_2$ is the combustion of fossil fuels such as coal, natural gas, and oil for energy and transportation. Using conventional energy sources leaves a vast carbon footprint on our environment. Moreover, an excess amount of $CO_2$ in the atmosphere has an adverse impact on the climate and living organisms, such as severe weather change, food shortage, and migration of animals. Therefore, several techniques and measures have been undertaken to mitigate $CO_2$ emissions and look for and develop new energy alternatives to curb such a growing adverse scenario. Among such measures are the conversion of $CO_2$ into value-added products and carbon dioxide capture and sequestration technologies. However, from a practical and more economical point of view, converting $CO_2$ into value-added products such as N, N-dimethylformamide, dimethoxyethane, formic acid, and methanol is seen as a viable solution to $CO_2$ mitigation. Among these value-added products, some economically interesting and environmentally acceptable products generated from $CO_2$ conversion are methane and benzimidazole. However, due to high thermodynamic stability and chemically inert nature, catalysts are required to activate the $CO_2$ for such chemical transformations. Therefore, several types of metal catalysts have been applied as competent materials for heterogeneous $CO_2$ methanation. However, most of these catalysts are expensive, and some need help with stability issues at elevated temperatures and pressure. Transitional metals have also been extensively used to design these catalysts instead of noble metals due to their expensive nature, low abundance, and limited industrial application. However, the monometallic transitional metal catalysts also suffer from deactivation, metal particle sintering, and regeneration of the catalysts.

Despite these recent advances, the drawbacks of each of the methods above indicate that there is still a need for effective catalysts for converting $CO_2$ into value-added products and methods of making such catalysts. More importantly, the challenge is that such methods should be cost-effective and rapid to attract industries to adopt these processes.

In view of the foregoing, one objective of the present disclosure is to provide a cost-efficient and economically viable method of making a bimetallic nanoalloy composite for overcoming the drawbacks above for $CO_2$ fixation. A second objective of the present disclosure is to describe a method of making a benzimidazole compound and methane from $CO_2$.

SUMMARY

In an exemplary embodiment, a method of making a bimetallic nanoalloy composite. The method includes mixing and dissolving a nickel salt, a cobalt salt, and an aromatic carboxylic acid in a first solvent to form a first mixture; mixing acetic acid with the first mixture and heating at a temperature of 150 to 200 degrees Celsius (° C.) form a second mixture; washing the second mixture with at least one organic solvent and drying to form a bimetallic metal-organic framework (CoNiBTC); heating the CoNiBTC at a temperature of 600 to 900° C. under a nitrogen stream to form a pyrolyzed composite; cooling the pyrolyzed composite and exposing to a gas mixture to form the bimetallic nanoalloy composite. In some embodiments, the bimetallic nanoalloy composite is in the form of bimetallic nanoalloy composite particles comprising cobalt nanoparticles, nickel nanoparticles and porous carbon layers. In some embodiments, the cobalt nanoparticles present in the bimetallic nanoalloy composite have an average particle size of 5 to 50 nanometers (nm). In some embodiments, the nickel nanoparticles present in the bimetallic nanoalloy composite have an average particle size of 5 to 50 nm. In some embodiments, the nanoparticles of cobalt and nickel are embedded in the porous carbon layers of the bimetallic nanoalloy composite and are uniformly distributed throughout the bimetallic nanoalloy composite.

In some embodiments, the cobalt nanoparticles are present in the bimetallic nanoalloy composite at a concentration of 20 to 50% by weight based on the total weight of the bimetallic nanoalloy composite. In another embodiment, the nickel nanoparticles are present in the bimetallic nanoalloy composite at a concentration of 10 to 30% by weight based on the total weight of the bimetallic nanoalloy composite.

In some embodiments, the bimetallic nanoalloy composite is in the form of particles having a surface area of 150 to 210 square meters per gram ($m^2/g$). In another exemplary embodiment, the lattice structure of the bimetallic nanoalloy composite has an average interplanar spacing of 0.05 to 0.5 nm.

In some embodiments, the nickel salt includes nickel sulfate, nickel acetate, nickel chloride, nickel nitrate, nickel carbonate, nickel phosphate and nickel oxalate, and/or a hydrate thereof. In one example, the cobalt salt includes cobalt sulfate, cobalt acetate, cobalt citrate, cobalt iodide, cobalt chloride, cobalt perchlorate, cobalt nitrate, cobalt phosphate, cobalt triflate, cobalt bis(trifluoromethanesulfonyl)imide, cobalt tetrafluoroborate, cobalt bromide, and/or a hydrate thereof.

In some embodiments, the aromatic carboxylic acid includes at least one of trimesic acid, trimellitic acid, trimellitic anhydride, and pyromellitic acid anhydride.

In some embodiments, the solvent is an amide solvent selected from the group consisting of N-methyl-2-pyrrolidone, N,N-dimethylacetamide, N,N-dimethylformamide, and 1,3-dimethyl-2-imidazolidinone.

In some embodiments, a molar ratio of the nickel salt to the cobalt salt in a range of 1:10 to 10:1. In some embodiments, a molar ratio of the aromatic carboxylic acid to the combined amount of nickel and cobalt salt in the first mixture is in a range of 1:5 to 5:1.

In some embodiments, the bimetallic metal-organic framework (CoNiBTC) is in the form of particles having a surface area of 650 to 750 $m^2/g$.

In some embodiments, the gas mixture includes an oxygen gas and a nitrogen gas. In some embodiments, a flow rate ratio of the oxygen gas to the nitrogen gas in a range of 1:1 to 1:10.

In some embodiments, a method of making a benzimidazole compound is described. The method includes contacting a phenylenediamine compound with the bimetallic nanoalloy composite prepared by the above method, in the presence of $CO_2$ and $H_2$, and heating under a pressure of 20 to 40 bar to form the benzimidazole compound having a structure of formula (I)

[I]

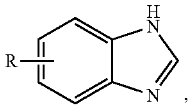

in which R is selected from the group including hydrogen, an optionally substituted alkyl, an optionally substituted cycloalkyl, an optionally substituted alkoxy, a hydroxyl group, a halogen group, a nitro group, and a cyano group.

In some embodiments, the method includes heating the CoNiBTC at a temperature in a range of 30 to 150° C. under a nitrogen stream to form the pyrolyzed composite. In some embodiments, the bimetallic nanoalloy composite has a concentration of 50 to 200 milligrams per millimole (mg/mmol) based on a total molar amount of the phenylenediamine compound. In some embodiments, the benzimidazole compound is at least one selected from the group including benzimidazole, 5-chloro-benzoimidazole, 5-methyl-benzoimidazole, and 5-nitro-benzoimidazole.

Aspects of the present disclosure are also related to a method of making methane from $CO_2$. The method includes heating the bimetallic nanoalloy composite prepared by the above method in a fix-bed reactor under a $N_2$ stream at a temperature of 500 to 600° C.; and introducing a first gas mixture stream of $H_2$ and $N_2$ to the fix-bed reactor in contact with the bimetallic nanoalloy composite to form a reduced composite. The method further includes cooling the reduced composite and introducing a second gas mixture stream of $CO_2$ and $H_2$ in contact with the reduced composite under a pressure of 20 to 40 bar; followed by heating to a temperature of 300 to 450° C. to form the methane.

In some embodiments, the method includes a flow rate ratio of the $H_2$ and the $N_2$ in the first gas mixture stream in a range of 1:2 to 1:20. In some embodiments, a flow rate ratio of the $CO_2$ and the $H_2$ in the second gas mixture stream is in a range of 10:1 to 1:1.

In an exemplary embodiment, the present invention relates to the use of a fix bed reactor in the form of a vertical cylindrical reactor for making methane. The reactor includes a top portion, a vertically oriented cylindrical body portion, a bottom portion and a housing having an open top and open bottom supportably maintained with the vertically oriented cylindrical body portion. The bimetallic nanoalloy composite is supportably retained within the housing, permitting fluid flow therethrough. The reactor includes at least one propeller agitator disposed in the bottom portion, with the bottom portion cone-shaped or pyramidal. The reactor further includes a plurality of recirculation tubes fluidly connecting the bottom portion of the vertical cylindrical reactor with the body portion of the vertical cylindrical reaction.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
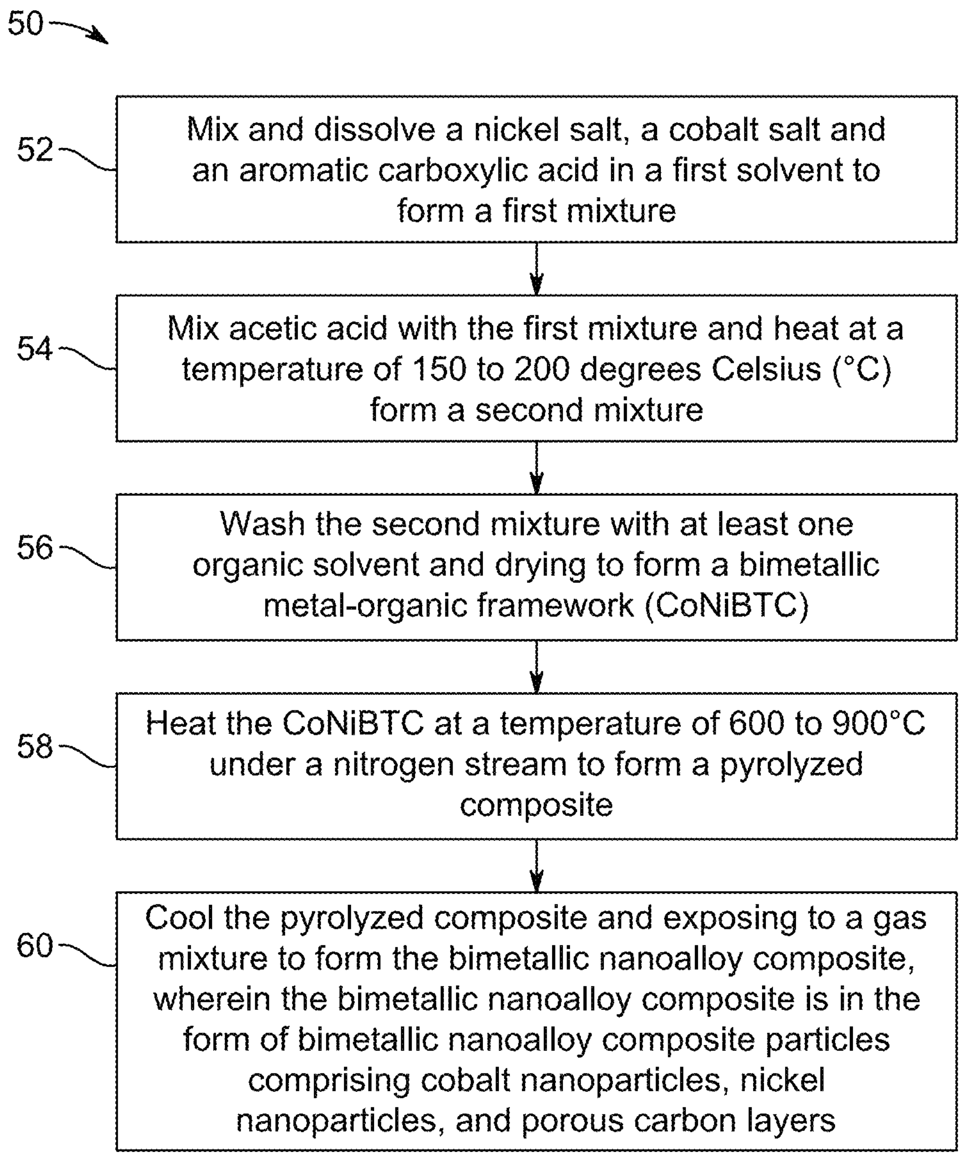
FIG. 1A is a flowchart depicting a method of making a bimetallic nanoalloy composite; according to certain embodiments.

When describing the present disclosure, the terms used are to be construed in accordance with the following definitions, unless a context dictates otherwise. Embodiments of the present invention will now be described more fully hereinafter with reference to the accompanying drawings wherever applicable, in which some, but not all embodiments of the disclosure are shown.

Further, as used herein, the use of singular includes plural and the words ‘a’, ‘an’ includes ‘one’ and means ‘at least one’ unless otherwise stated in this application.

Furthermore, the terms “approximately”, “approximate”, “about,” and similar terms generally refer to ranges that include the identified value within a margin of 20%, 10%, or preferably 5%, and any values therebetween.

The use of the terms “include,” “includes”, “including,” “have,” “has,” or “having” should be generally understood as open-ended and non-limiting unless specifically stated otherwise.

The terms ‘elements’ and ‘components’ include a single unit as well as more than a single unit unless specified otherwise.

The terms “compound” and “derivative” as used herein, are used interchangeably, and refer to a chemical entity, whether in the solid, liquid, or gaseous phase, and whether in a crude mixture or purified and isolated.

The term “compounds” as used herein, refers to include the compounds disclosed in the present invention disclosure, salts, solvates, and salts of solvates, and mixtures, known and unknown variations and forms thereof.

As used herein, “metal organic framework” or “MOF” includes a class of porous materials consisting of linkers (also “organic ligands” or “connectors”) coordinated to metals resulting in a 1-dimensional, 2-dimensional, or 3-dimensional structure with well-defined and repeated structural characteristics throughout the material.

The term “drying” as used herein, refers to a method of removing solvent and/or water or any moisture from the compounds of the invention and/or composite, which, unless otherwise specified, may be done at atmospheric pressure or under reduced pressure and with or without heating until the level of solvent and/or water contained reached an acceptable level.

The term “alkyl” or “alkyl groups,” as used herein, refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or “cycloalkyl” or “alicyclic” or “carbocyclic” groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl substituted alkyl groups (e.g., alkyl-substituted cycloalkyl groups and cycloalkyl-substituted alkyl groups). The term “alkyl” includes both “unsubstituted alkyls” and “substituted alkyls.” As used herein, the term “substituted alkyls” refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups. In some embodiments, substituted alkyls can include a heterocyclic group.

As used herein, the term “heterocyclic group” includes closed ring structures analogous to carbocyclic groups in which one or more of the carbon atoms in the ring is an element other than carbon, for example, nitrogen, sulfur, or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Referring to FIG. 1A, a schematic flow diagram of the method 50 of making a bimetallic nanoalloy composite is illustrated. The order in which the method 50 is described is not intended to be construed as a limitation, and any number of the described method steps may be combined in any order to implement the method 50. Additionally, individual steps may be removed or skipped from the method 50 without departing from the spirit and scope of the present disclosure.

At step 52, the method 50 includes mixing and dissolving a nickel salt, a cobalt salt, and an aromatic carboxylic acid in a first solvent to form a first mixture. In an embodiment, the nickel salt may be one or more selected from nickel sulfate, nickel acetate, nickel chloride, nickel nitrate, nickel carbonate, nickel phosphate and nickel oxalate, and/or a hydrate thereof. In a preferred embodiment, the nickel salt may be nickel nitrate, and nickel nitrate hexahydrate. In another embodiment, the cobalt salt is one or more selected from cobalt sulfate, cobalt acetate, cobalt citrate, cobalt iodide, cobalt chloride, cobalt perchlorate, cobalt nitrate, cobalt phosphate, cobalt triflate, cobalt bis(trifluoromethane sulfonyl)imide, cobalt tetrafluoroborate, cobalt bromide, and/or a hydrates thereof. In a preferred embodiment, the cobalt salt may be cobalt nitrate and cobalt nitrate hexahydrate. In certain embodiments, a combination of nickel salts/cobalt salts may be used to prepare the bimetallic nanoalloy composite of the present disclosure. In some specific examples, a combination of nickel salt and cobalt salt may also be used. The nickel salt and cobalt salt so that a molar ratio of the nickel salt to the cobalt salt is in a range of 1:10 to 10:1, preferably 1:8 to 8:1, preferably 1:6 to 6:1, preferably 1:4 to 4:1, preferably 1:2 to 2:1, or even more preferably about 1:1. Other ranges are also possible.

In an embodiment, the aromatic carboxylic acid includes at least one of trimesic acid, trimellitic acid, trimellitic anhydride, and pyromellitic acid anhydride. In a preferred embodiment, the aromatic carboxylic acid is the trimesic acid. In a preferred embodiment, the aromatic carboxylic acid may be trimesic acid. In another embodiment, the first solvent is an amide solvent selected from the group consisting of N-methyl-2-pyrrolidone, N,N-dimethylacetamide, N,N-dimethylformamide (DMF), and 1,3-dimethyl-2-imidazolidinone. In a preferred embodiment, the first solvent may be DMF. Furthermore, a molar ratio of the aromatic carboxylic acid to the combined amount of nickel and cobalt salt in the first mixture is in a range of 1:5 to 5:1, preferably 1:3 to 3:1, or even more preferably about 1:1. Other ranges are also possible.

In some embodiments, the nickel salt is present in the first mixture at a concentration of 0.005 to 0.1 M, preferably 0.01 to 0.05 M, preferably 0.02 to 0.03 M, or even more preferably about 0.025 M. In some further embodiments, the cobalt salt is present in the first mixture at a concentration of 0.005 to 0.1 M, preferably 0.01 to 0.05 M, preferably 0.02 to 0.03 M, or even more preferably about 0.025 M. In some preferred embodiments, the aromatic carboxylic acid is present in the first mixture at a concentration of 0.005 to 0.1 M, preferably 0.01 to 0.08 M, preferably 0.02 to 0.06 M, or even more preferably about 0.05 M. Other ranges are also possible.

At step 54, the method 50 includes mixing acetic acid with the first mixture and heating at a temperature of 150 to 200 degrees Celsius (° C.) to form a second mixture. In an embodiment, the heating is carried out at a temperature of 150, preferably at 155, preferably at 160, preferably at 160, preferably at 165, preferably at 170, preferably at 175, preferably at 180, preferably at 185, preferably at 190, preferably at 195 to about 200° C. to form a second mixture for 2 to about 4 days. In a preferred embodiment, the acetic acid is heated with the first mixture at a temperature of between 170° C. to 180° C., preferably at 175° C. for 72 hours. In some embodiments, a volume ratio of the acetic acid to the first mixture is in a range of 1:10 to 1:1, preferably 1:8 to 1:2, preferably 1:6 to 1:3, or even more preferably about 1:4. Other ranges are also possible.

At step 56, the method 50 includes washing the second mixture with at least one organic solvent and drying to form a bimetallic metal-organic framework (CoNiBTC). The CoNiBTC is in the form of particles having a surface area of 650 to 750 $m^2/g$, preferably 670 to 730 $m^2/g$, or even more preferably 690 to 710 $m^2/g$. In a specific embodiment, the surface area of CoNiBTC is 710 $m^2/g$. Other ranges are also possible.

Figure 8:
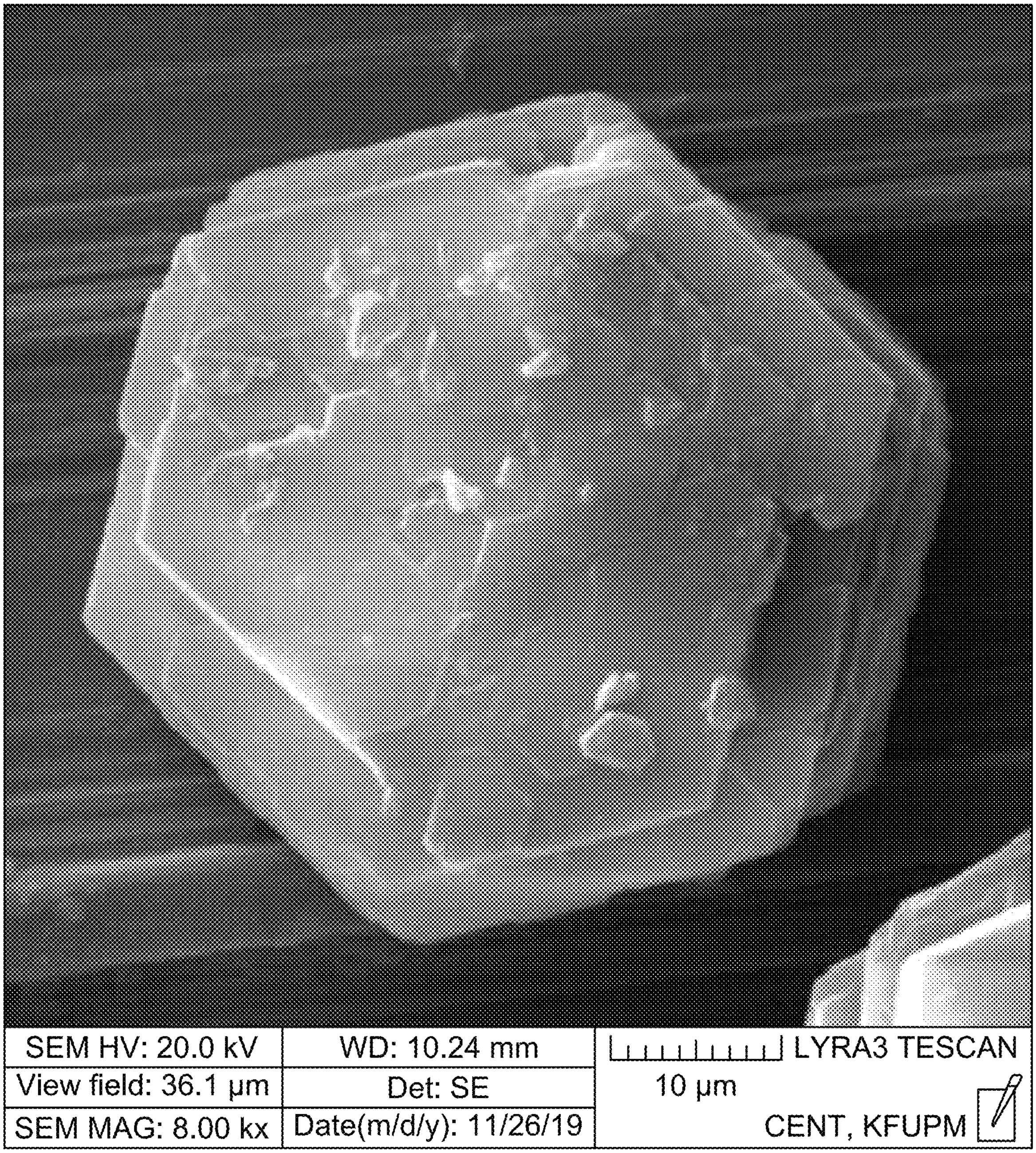
FIG. 8 shows a field emission scanning electron microscope (FESEM) of bimetallic CoNiBTC with hexagonal-shaped layered microcrystalline materials; according to certain embodiments.
Figure 11:
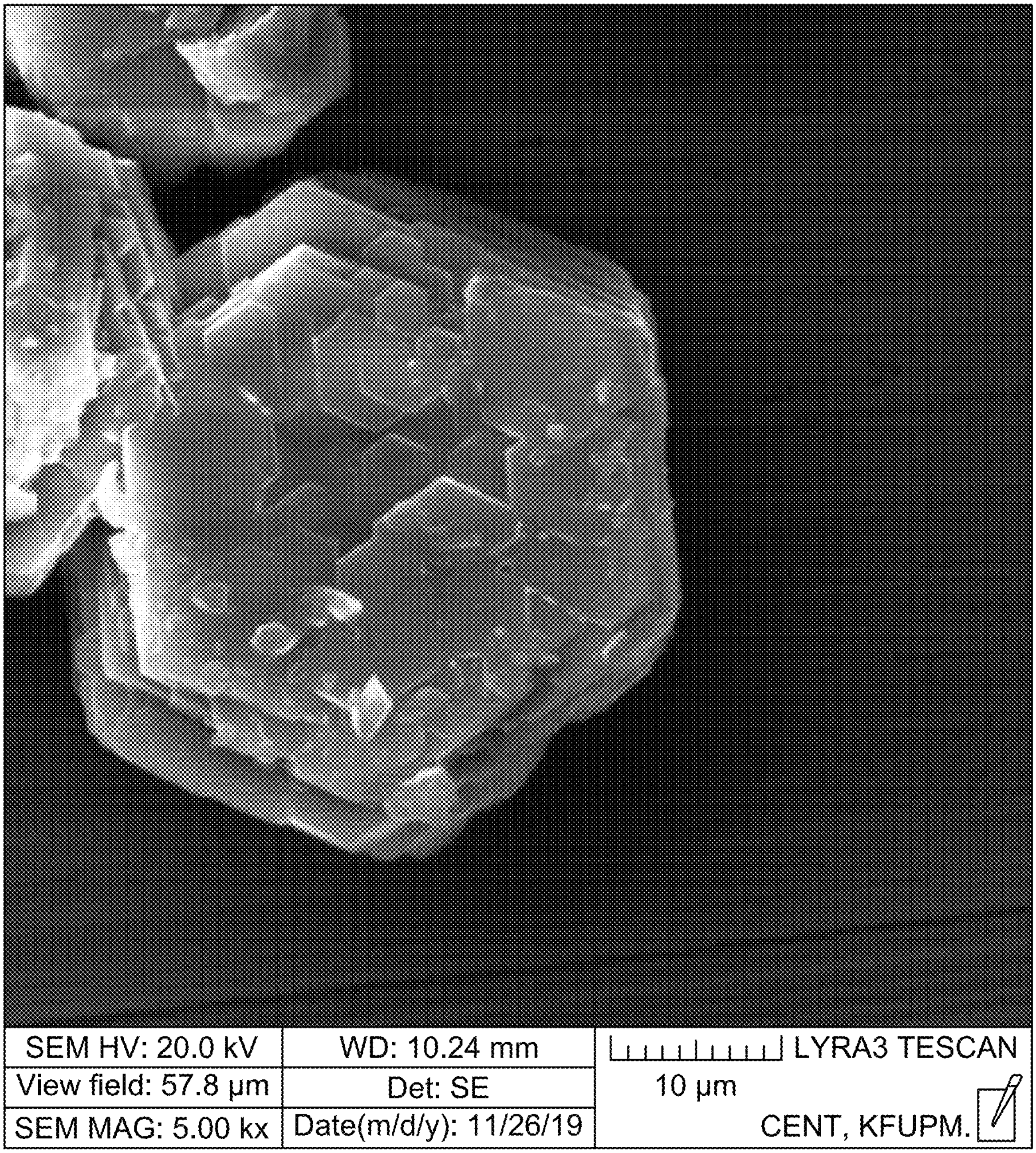
FIG. 11 shows FESEM of bimetallic CoNiBTC-1, according to certain embodiments.
Figure 13:
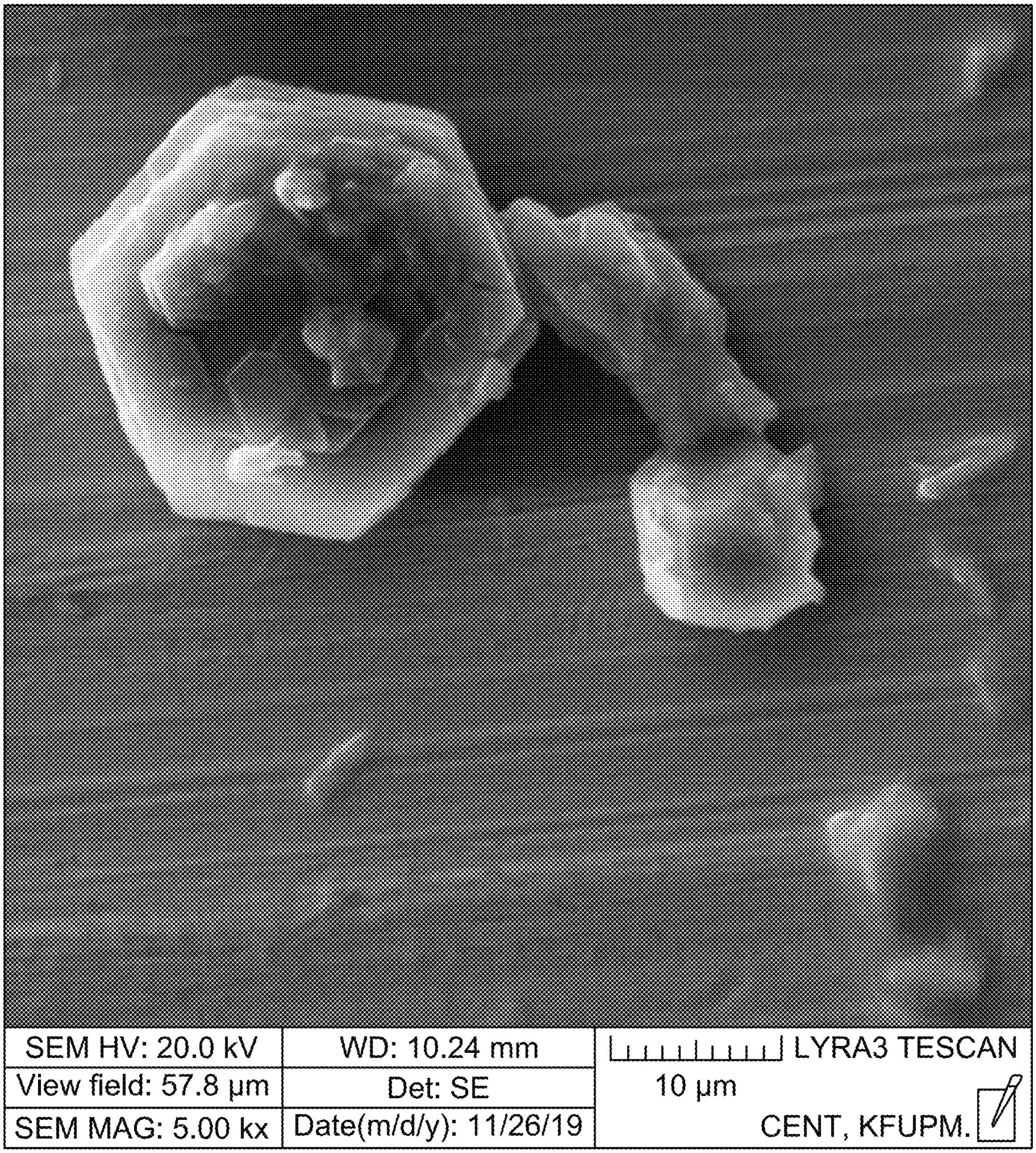
FIG. 13 shows FESEM of bimetallic CoNiBTC-2, according to certain embodiments.

Referring to FIGS. 8, 11, and 13, FESEM images of bimetallic metal-organic frameworks (CoNiBTC). The CoNiBTC is a hexagonal-shaped layered microcrystalline having an average circumradius radius in a range of 10 to 50 m, preferably 15 to 45 m, preferably 20 to 40 m, preferably 25 to 35 m, or even more preferably about 30 m.

At step 58, the method 50 includes heating the CoNiBTC at a temperature of 600 to 900° C. under a nitrogen stream to form a pyrolyzed composite. In some embodiments, the CoNiBTC is heated at 600, preferably at 650, preferably at 700, preferably at 750, preferably at 800, preferably at 850 to about 900° C. In a specific embodiment, the CoNiBTC is heated to 750° C. for about 5 to 10 hours. In an embodiment, the CoNiBTC is heated under the nitrogen stream for 1 to 5 hours, preferably 2-4 hours, more preferably 2 hours. In a specific embodiment, the pyrolyzed composite is exposed to the gas mixture including an oxygen gas and a nitrogen gas for 1 to 3 hours, preferably 1.5 to 2.5 h, or even more preferably about 2 h. A flow rate ratio of the oxygen gas to the nitrogen gas is in a range of 1:1 to 1:10, preferably 1:3 to 1:7, or even more preferably about 1:5. Other ranges are also possible.

At step 60, the method 50 includes cooling the pyrolyzed composite and exposing to a gas mixture to form the bimetallic nanoalloy composite. The bimetallic nanoalloy composite is in the form of bimetallic nanoalloy composite particles, including cobalt nanoparticles, nickel nanoparticles and porous carbon layers. The cobalt nanoparticles present in the bimetallic nanoalloy composite have an average particle size of 5 to 50 nanometers (nm), preferably 10 to 40 nm, preferably 20 to 30 nm, or even more preferably about 25 nm. The nickel nanoparticles present in the bimetallic nanoalloy composite have an average particle size of 5 to 50 nm, preferably 10 to 40 nm, preferably 20 to 30 nm, or even more preferably about 25 nm. Other ranges are also possible. The nanoparticles of cobalt and nickel are embedded in the porous carbon layers of the bimetallic nanoalloy composite and are uniformly distributed throughout the bimetallic nanoalloy composite.

In some embodiments, the cobalt nanoparticles are present in the bimetallic nanoalloy composite at a concentration of 20, preferably 25, preferably 30, preferably 35, preferably 40, and preferably 45 to about 50% by weight based on the total weight of the bimetallic nanoalloy composite. In some embodiments, the nickel nanoparticles are present in the bimetallic nanoalloy composite at a concentration of 20, preferably 25 to about 30% by weight based on the total weight of the bimetallic nanoalloy composite. In some embodiments, the cobalt nanoparticles are present in the bimetallic nanoalloy composite at a concentration of up to 50% by weight based on the total weight of the bimetallic nanoalloy composite; and the nickel nanoparticles are present in the bimetallic nanoalloy composite at a concentration of up to 30% by weight based on the total weight of the bimetallic nanoalloy composite.

The bimetallic nanoalloy composite prepared by the method of the present disclosure is in the form of particles having a surface area of 150 to 210 square meters per gram ($m^2/g$). In some embodiments, the bimetallic nanoalloy composite is in the form of particles having a surface area of 150, preferably 155, preferably 160, preferably 165, preferably 170, preferably 175, preferably 180, preferably 185, preferably 190, preferably 195, preferably 200, preferably 205 to about 200 $m^2/g$. In another embodiment, the lattice structure of the bimetallic nanoalloy composite has an average interplanar spacing of 0.05 to 0.5 nm. In an embodiment, the bimetallic nanoalloy composite prepared by the method of the present disclosure is in the form of particles having a surface area of 150 to 210 square meters per gram ($m^2/g$). In another embodiment, the lattice structure of the bimetallic nanoalloy composite has an average interplanar spacing of 0.05 to 0.5 nm.

The bimetallic nanoalloy composite (CoNi@C) and the CoNiBTC were evaluated by powdered X-ray diffraction (PXRD), Fourier Transform Infra-Red spectroscopy (FTIR), surface area porosity analyzer, X-ray photoelectron spectroscopy (XPS), field emission scanning electron microscopy (FESEM), transmission electron microscopy (TEM), hydrogen temperature-Programmed Reduction ($H_2$-TPR), $CO_2$ temperature-programmed desorption ($CO_2$-TPD), and inductively coupled plasma mass spectrometry (ICP-MS). Temperature program reduction uses $H_2$ ($H_2$-TPR), and $N_2$ adsorption/desorption method for calculating the structure, reducibility/$N_2$ uptake of the bimetallic nanoalloy composite (CoNi@C) and the CoNiBTC.

As used herein, the term "inductively coupled plasma mass spectrometry," or "ICP-MS" generally refers to a technique used to determine the elemental composition of a sample, such as a bimetallic nanoalloy composite. In some embodiments, the bimetallic nanoalloy composite is ionized and excited in an inductively coupled plasma (ICP), which is a high-temperature argon gas plasma generated by an electrical discharge. In some further embodiments, the ions are separated and detected based on their mass-to-charge ratio.

Temperature programmed desorption (TPD) is a technique used to monitor surface interactions between molecular species on a surface when the surface temperature has changed in a controlled setting. This technique determines the strength of interactions between the bimetallic nanoalloy composite, and the transition metals adsorbed on the bimetallic nanoalloy composite. This is done by placing the bimetallic nanoalloy composite inside a reactor and pushing an inert gas into the chamber. Alternatively, the sample can be located in an ultra-high vacuum (UHV) chamber with no carrier gas. The sample is dosed with a probe gas such as CO, $NH_3$, $H_2$, etc. The sample is then increased in temperature at a linear ramp rate, and the desorption products are analyzed by a mass spectrometer.

As used herein, the term "$N_2$ adsorption/desorption method" generally refers to a technique used to measure the specific surface area of a solid material, such as a bimetallic nanoalloy composite. In some embodiments, the bimetallic nanoalloy composite is exposed to a stream of nitrogen gas at low temperature and pressure. The nitrogen gas is adsorbed onto the surface of the bimetallic nanoalloy composite, filling the pores and creating a monolayer of adsorbed nitrogen. In some further embodiments, the amount of nitrogen adsorbed at a given pressure is measured using a gas adsorption instrument, such as a BET instrument. In some preferred embodiments, the BET analysis is performed on a BELCAT II analyzer manufactured by Microtrack Bell Co., Ltd. In some more preferred embodiments, the nitrogen gas is gradually removed from the bimetallic nanoalloy composite, causing the desorption of the adsorbed nitrogen. The amount of nitrogen desorbed at a given pressure is also measured using the gas adsorption instrument. By analyzing the amount of nitrogen adsorbed and desorbed, the specific surface area of the bimetallic nanoalloy composite can be calculated using the BET (Brunauer-Emmett-Teller) and Barrett, Joyner and Halenda (BJH) equation.

The bimetallic nanoalloy composite was characterized by various analytical techniques, one among which is hydrogen temperature-programmed reduction ($H_2$-TPR). As used herein, the term "temperature program reduction using $H_2$," or "$H_2$-TPR" generally refers to a technique used to study the reducibility of a solid material, such as a bimetallic nanoalloy composite, by measuring the consumption of a reducing gas, such as hydrogen, as a function of temperature. In some embodiments, the bimetallic nanoalloy composite is first heated in an oxidizing gas, such as air or oxygen, to remove any adsorbed species and to convert the bimetallic nanoalloy composite to an oxide. In some further embodiments, the oxidized bimetallic nanoalloy composite is then cooled down and exposed to a stream of hydrogen gas, while the temperature is gradually increased. As the temperature increases, the hydrogen reacts with the oxidized bimetallic nanoalloy composite, causing a reduction of the material. In some preferred embodiments, this reduction reaction may be exothermic, and the heat generated by the reaction is monitored as a function of temperature.

Figure 7A:
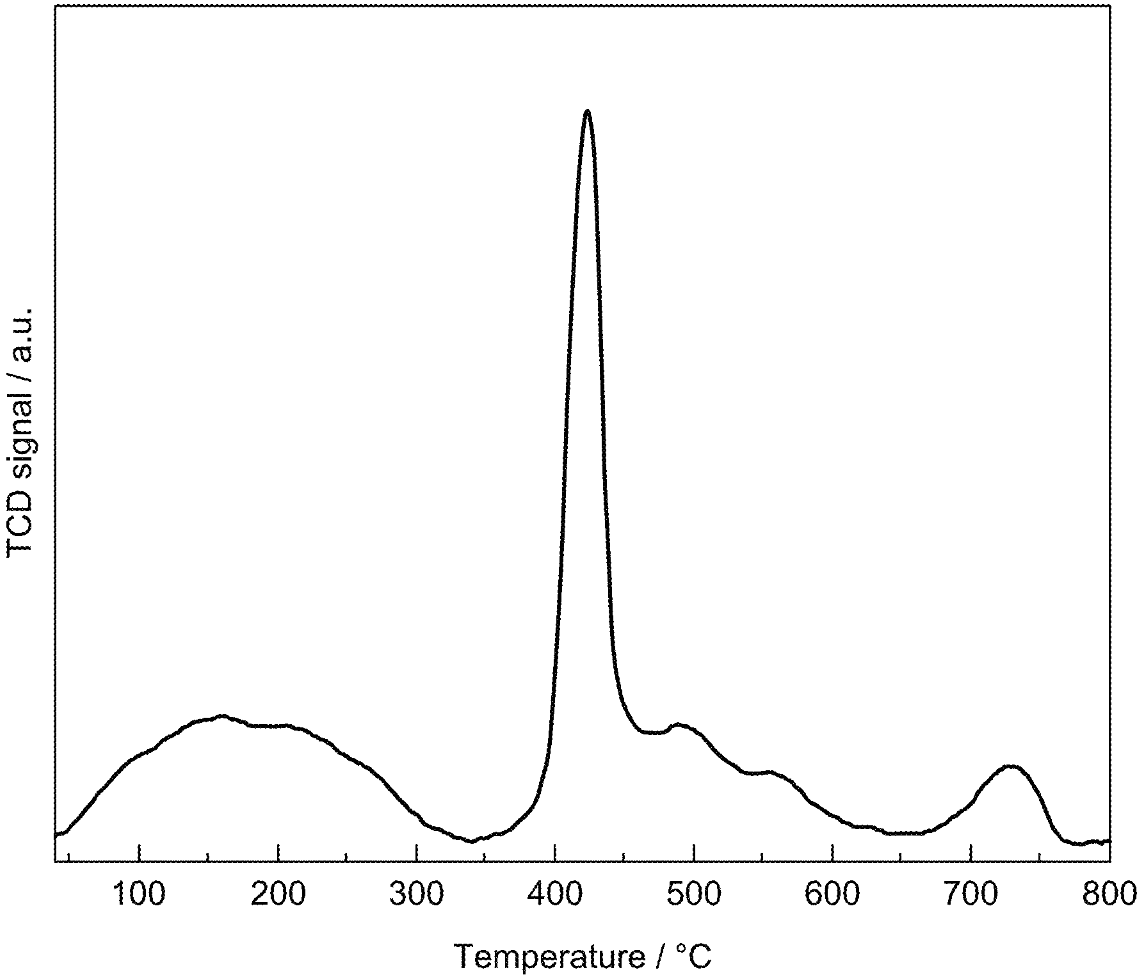
FIG. 7A shows a $CO_2$ Temperature-Programmed Desorption ($CO_2$-TPD) of CoNi@C; according to certain embodiments.
Figure 7B:
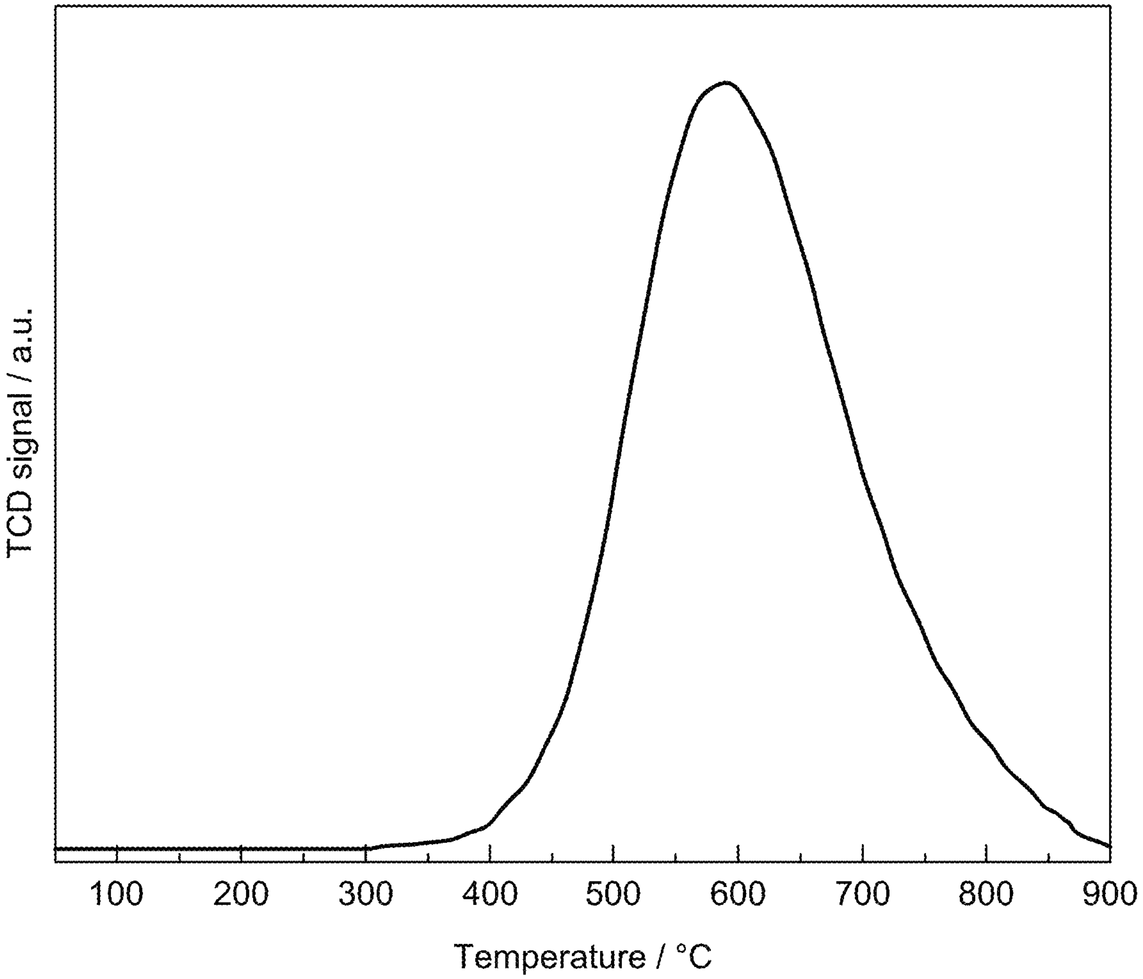
FIG. 7B shows a Hydrogen Temperature-Programmed Reduction ($H_2$-TPR) of CoNi@C; according to certain embodiments.

In some embodiments, the $H_2$-TPR was conducted on a BellCat II chemisorption analyzer. The bimetallic nanoalloy composite was placed in a quartz calcined at a temperature of 400 to 800° C., preferably 450 to 750° C., preferably 500 to 700° C., preferably 550 to 650° C., or even more preferably about 600° C. under an argon flow for at least 30 minutes, at least 60 minutes, at least 120 minutes. In some further embodiments, the bimetallic nanoalloy composite was cooled to a temperature of no more than 70° C., preferably no more than 60° C., or even more preferably no more than 50° C. In some preferred embodiments, a gas flow contains hydrogen ($H_2$) and argon (Ar) in a volumetric ratio of $H_2$ to Ar ranging from 1:20 to 1:1, preferably 1:15 to 1:5, or even more preferably about 1:10 was introduced to flow over the bimetallic nanoalloy composite at a flow rate of 10 to 60 cubic centimeters per minutes ($cm^3$/min), preferably 20 to 50 $cm^3$/min, or even more preferably about 30 $cm^3$/min. In some preferred embodiments, the temperature of the analyzer containing the bimetallic nanoalloy composite was increased at ramping rate of 5 to 20° C. per minute (° C./min) until the temperature reaches about 700 to 1200° C., or even more preferably about 900° C. Other ranges are also possible. In some most preferred embodiments, the bimetallic nanoalloy composite of the present disclosure has at least one peak in a range of 400 to 850° C., preferably 500 to 700° C., or even more preferably about 590° C., as depicted in FIG. 7B. Other ranges are also possible.

As used herein, the term "temperature program desorption using carbon dioxide," or "$CO_2$-TPD" generally refers to a technique used to study the surface acidity of a solid material, such as a bimetallic nanoalloy composite. In some embodiments, the bimetallic nanoalloy composite is first heated in an inert gas, such as nitrogen, to remove any adsorbed species and to stabilize the surface. In some embodiments, the bimetallic nanoalloy composite is then cooled down and exposed to a stream of carbon dioxide gas, which is adsorbed onto the surface of the bimetallic nanoalloy composite. The amount of carbon dioxide adsorbed is proportional to the surface acidity of the bimetallic nanoalloy composite. The bimetallic nanoalloy composite is then heated at a constant rate while the amount of carbon dioxide desorbed is monitored as a function of temperature. In some further embodiments, as the temperature increases, the adsorbed carbon dioxide begins to desorb from the surface of the bimetallic nanoalloy composite. In some preferred embodiments, the desorption of carbon dioxide may be exothermic, and the heat generated by the desorption process is monitored using a thermal conductivity detector.

In some embodiments, the $CO_2$-TPD is performed by saturating the bimetallic nanoalloy composite in a $CO_2$ atmosphere at a temperature of 25 to 65° C., preferably about 45° C. In some further embodiments, the bimetallic nanoalloy composite after saturation was flushed with a carrier gas for 5 to 60 min, or even more preferably about 30 min to remove physically adsorbed $CO_2$. In some more preferred embodiments, the bimetallic nanoalloy composite after saturation was heated to a temperature of 600 to 800° C., or even more preferably about 700° C. to desorb $CO_2$. In some preferred embodiments, the bimetallic nanoalloy composite of the present disclosure has at least a first peak in a range of 50 to 350° C., preferably 100 to 250° C., or even more preferably about 150° C., as depicted in FIG. 7A. In some most preferred embodiments, the bimetallic nanoalloy composite of the present disclosure has at least a second peak in a range of 350 to 550° C., preferably 400 to 500° C., or even more preferably about 425° C., as depicted in FIG. 7A. Other ranges are also possible.

Figure 2A:
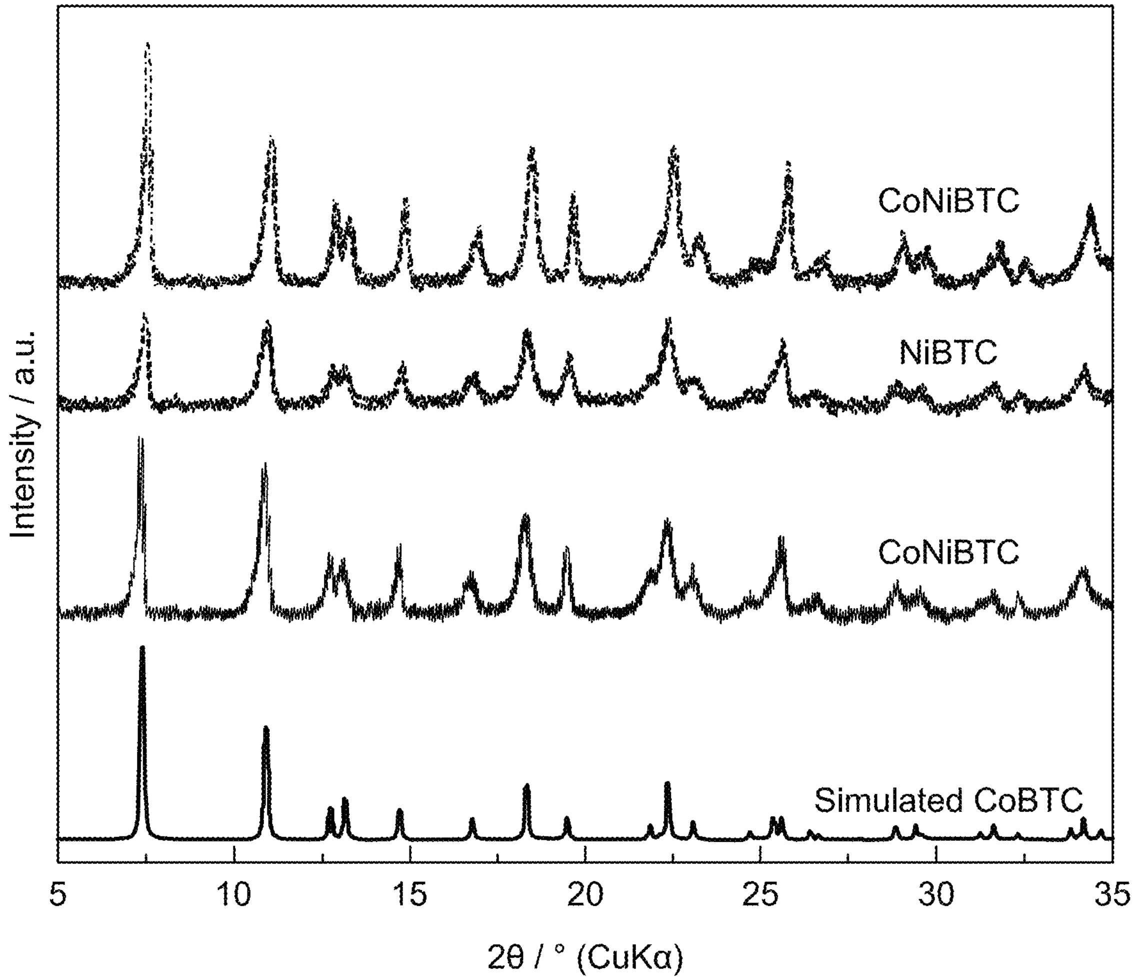
FIG. 2A shows powdered X-ray diffraction (PXRD) of nickel (Ni) derived from a bimetallic metal-organic framework (MOF) (CoNiBTC), CoBTC, and NiBTC; according to certain embodiments.
Figure 2B:
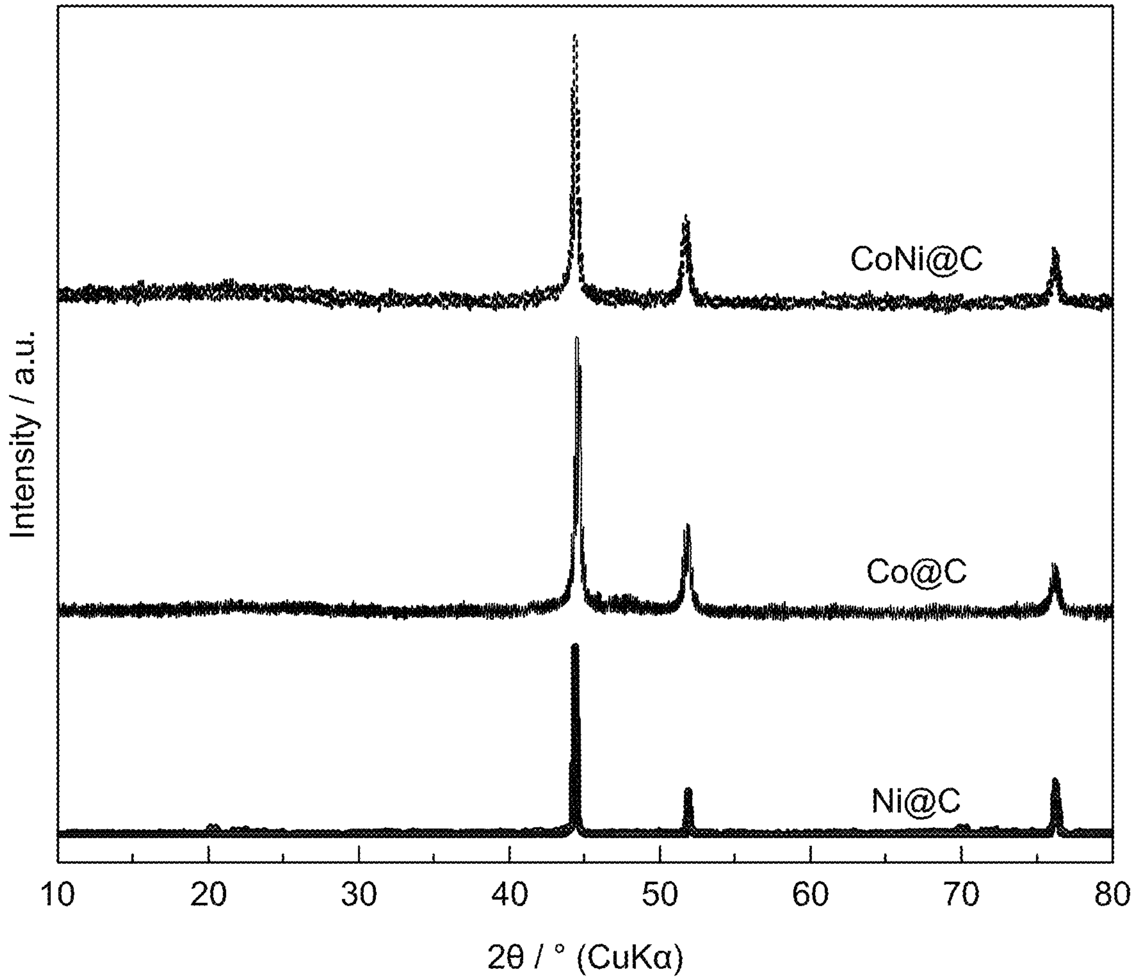
FIG. 2B shows a PXRD of CoNi@C, Ni@C, and Co@C; according to certain embodiments.
Figure 2C:
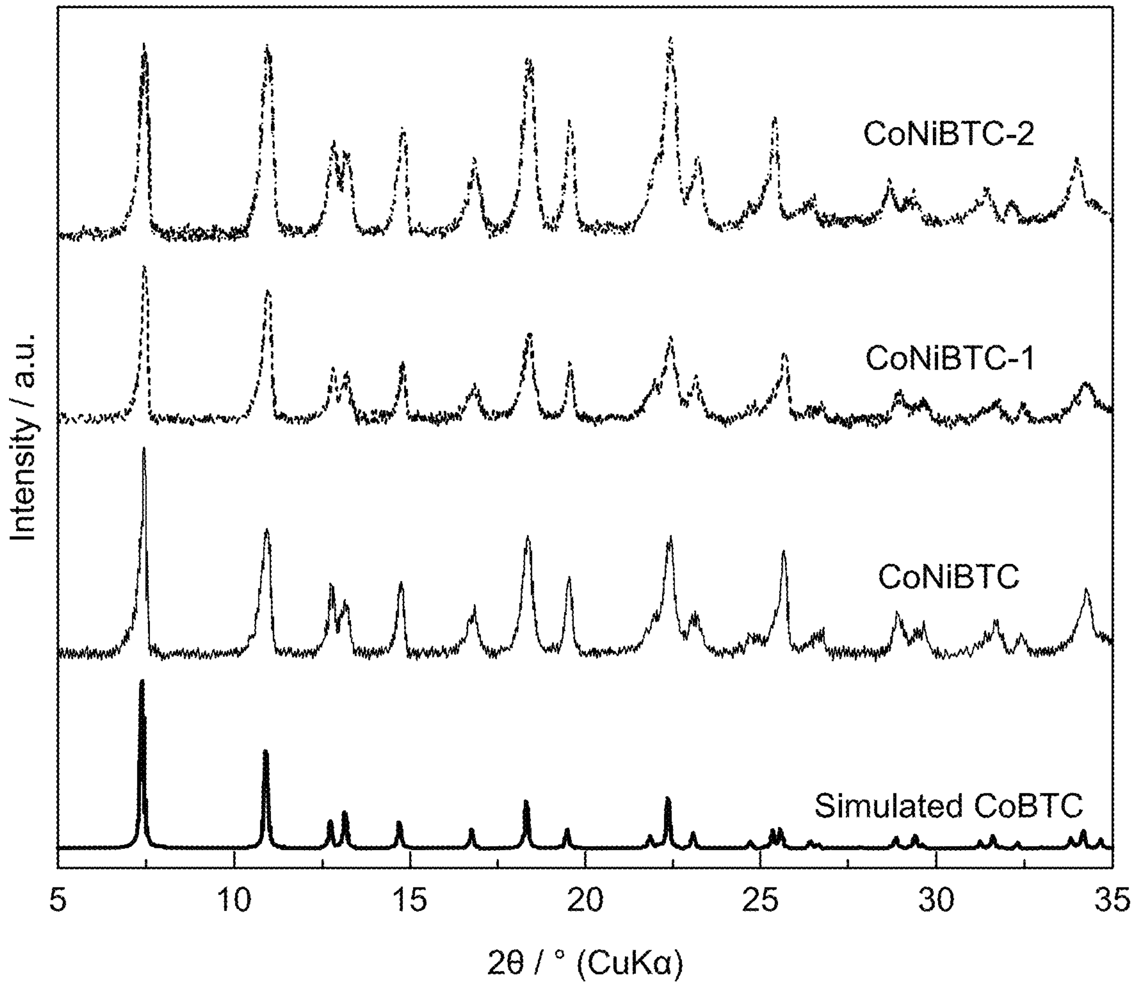
FIG. 2C shows PXRD of CoNiBTC, CoNiBTC-1, and CoNiBTC-2, according to certain embodiments.
Figure 2D:
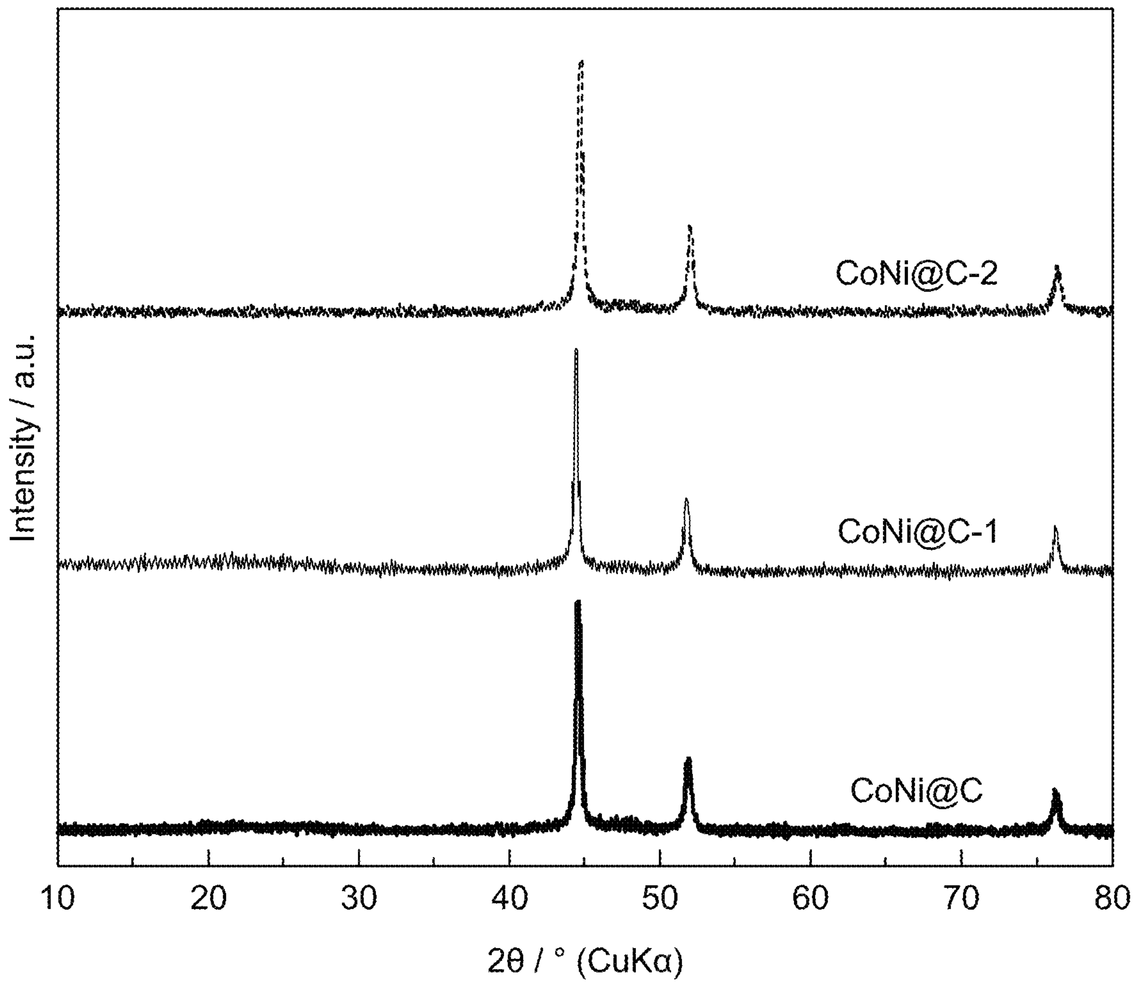
FIG. 2D shows a PXRD of CoNi@C, CoNi@C-1, and CoNi@C-2; according to certain embodiments.

The crystalline structures of the bimetallic nanoalloy composite (CoNi@C) and the CoNiBTC may be characterized by powder X-ray diffraction (P-XRD), respectively. In some embodiments, the XRD patterns are collected in a Rigaku MiniFlex diffractometer equipped with a Cu-Kα radiation source (λ=0.15406 nm) for a 20 range extending between 5 and 80°, preferably 15 and 70°, further preferably 30 and 600 at an angular rate of 0.005 to 0.04° $s^{-1}$, preferably 0.01 to 0.03° $s^{-1}$, or even preferably 0.02° $s^{-1}$. In some embodiments, the bimetallic nanoalloy composite has at least a first intense peak with a 2 theta (0) value in a range of 5 to 10°, preferably about 7.5°; at least a second intense peak with a 20 in a range of 10 to 12°, preferably about 11.5°; at least a third intense peak with a 20 in a range of 12 to 15°, preferably about 12.5 to 14°; at least a fourth intense peak with a 20 in a range of 16 to 20°, preferably 17 to 19°; at least a fifth intense peak with a 20 in a range of 20 to 35°, preferably 22.5 to 30°, as depicted in FIGS. 2A and 2B. Other ranges are also possible.

Figure 3:
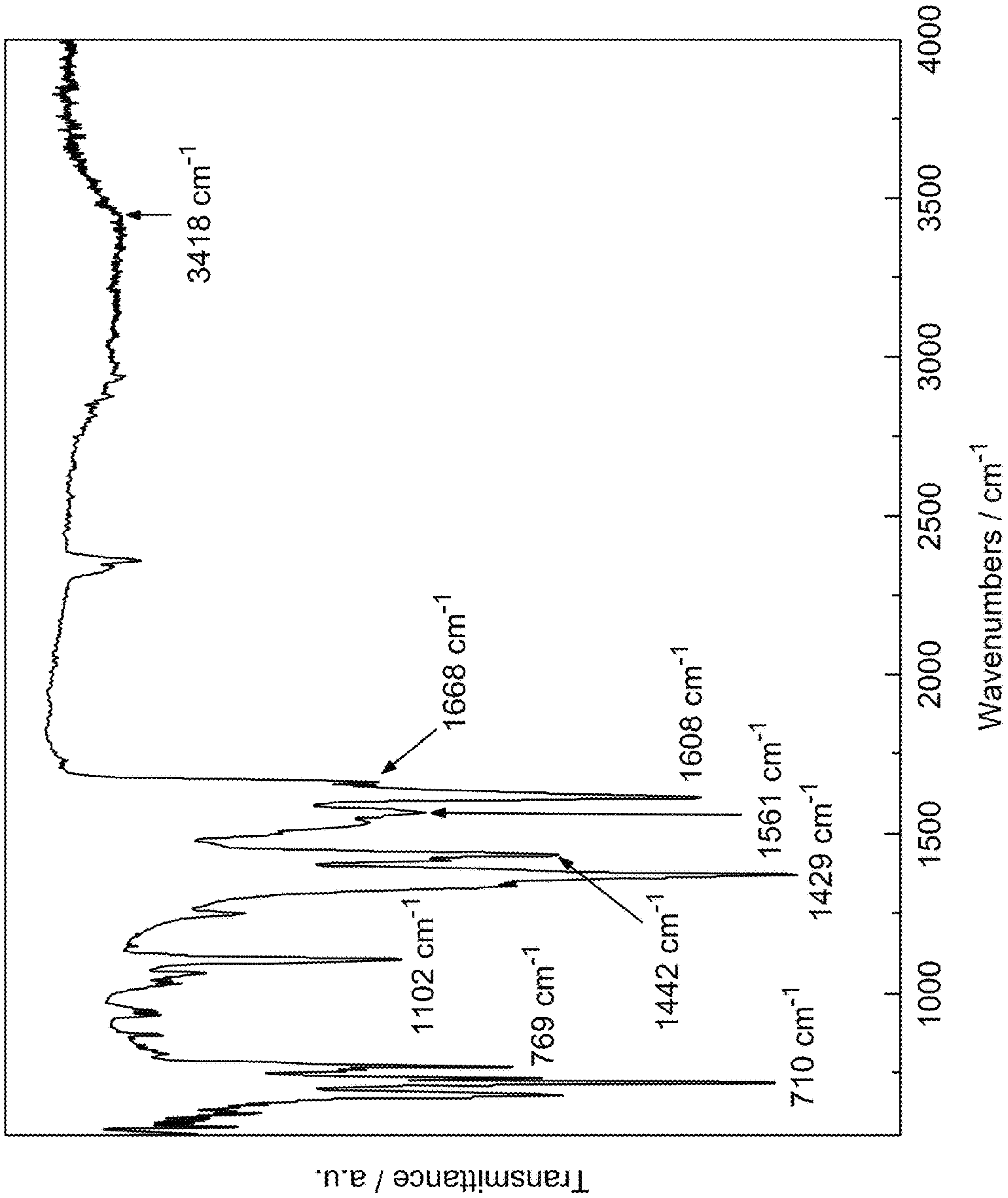
FIG. 3 shows a Fourier Transform Infra-Red spectroscopy (FTIR) spectrum of CoNiBTC; according to certain embodiments.

The structures of the bimetallic nanoalloy composite (CoNi@C) may be characterized by Fourier transforms infrared spectroscopy (FT-IR). In some embodiments, the FT-IR are collected in a Nicolet 6700 Thermo Scientific instrument acquired in a range of 4000 to 400 centimeter inverse ($cm^{-1}$) at 4 $cm^{-1}$ resolution. 20 scans were carried out for each sample. In some embodiments, the bimetallic nanoalloy composite (CoNi@C) has peaks at 800 to 1000 $cm^{-1}$, 1100 to 1700 $cm^{-1}$, and about 3500 $cm^{-1}$ in a Fourier transform infrared spectrum (FT-IR), as depicted in FIG. 3. Other ranges are also possible.

Aspects of the invention of the present disclosure include a method of making a benzimidazole compound. The method includes contacting a phenylenediamine compound with the bimetallic nanoalloy composite prepared by the method of the present invention, in the presence of $CO_2$ and $H_2$, and heating under a pressure of 20 to 40 bar to form the benzimidazole compound having a structure of formula (I)

[I]

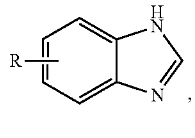
, wherein R is selected from the group consisting of hydrogen, an optionally substituted alkyl, an optionally substituted cycloalkyl, an optionally substituted alkoxy, a hydroxyl group, a halogen group, a nitro group, and a cyano group.

The heating is performed at a temperature in a range of 30, preferably 35, preferably 40, preferably 45, preferably 50, preferably 55, preferably 60, preferably 65, preferably 70, preferably 75, preferably 80, preferably 85, preferably 90, preferably 95, preferably 100, preferably 105, preferably 110, preferably 115, preferably 120, preferably 125, preferably 130, preferably 135, preferably 140, preferably 145 or about 150° C.

In some embodiments, the bimetallic nanoalloy composite has a concentration of 50, preferably 55, preferably 60, preferably 65, preferably 70, preferably 75, preferably 80, preferably 85, preferably at 90, preferably 95, preferably 100, preferably 105, preferably 110, preferably 125, preferably 120, preferably 125, preferably 130, preferably 135, preferably 140, preferably 145, preferably 150, preferably 155, preferably 160, preferably 165, preferably 170, preferably 175, preferably 180, preferably 185, preferably 190, preferably 195 or about 200 mg/mmol based on the total molar amount of the phenylenediamine compound.

In some embodiments, the heating is performed under a pressure of 20 to 40 bar, preferably 25 to 35 bar, or even more preferably about 30 bar. In some further embodiments, a volume ratio of the $CO_2$ to the $H_2$ is in a range of 10:1 to 1:10, preferably 1:7 to 7:1, preferably 1:4 to 4:1, or even more preferably about 1:1. Other ranges are also possible.

In yet another embodiment, the benzimidazole compound is at least one selected from the group consisting of benzimidazole, 5-chloro-benzoimidazole, 5-methyl-benzoimidazole, and 5-nitro-benzoimidazole. In some embodiments, a combination of the benzimidazole compounds or derivatives or precursors of the benzimidazole compound can be selected to prepare the benzimidazole compound by the method of present disclosure.

Figure 1B:
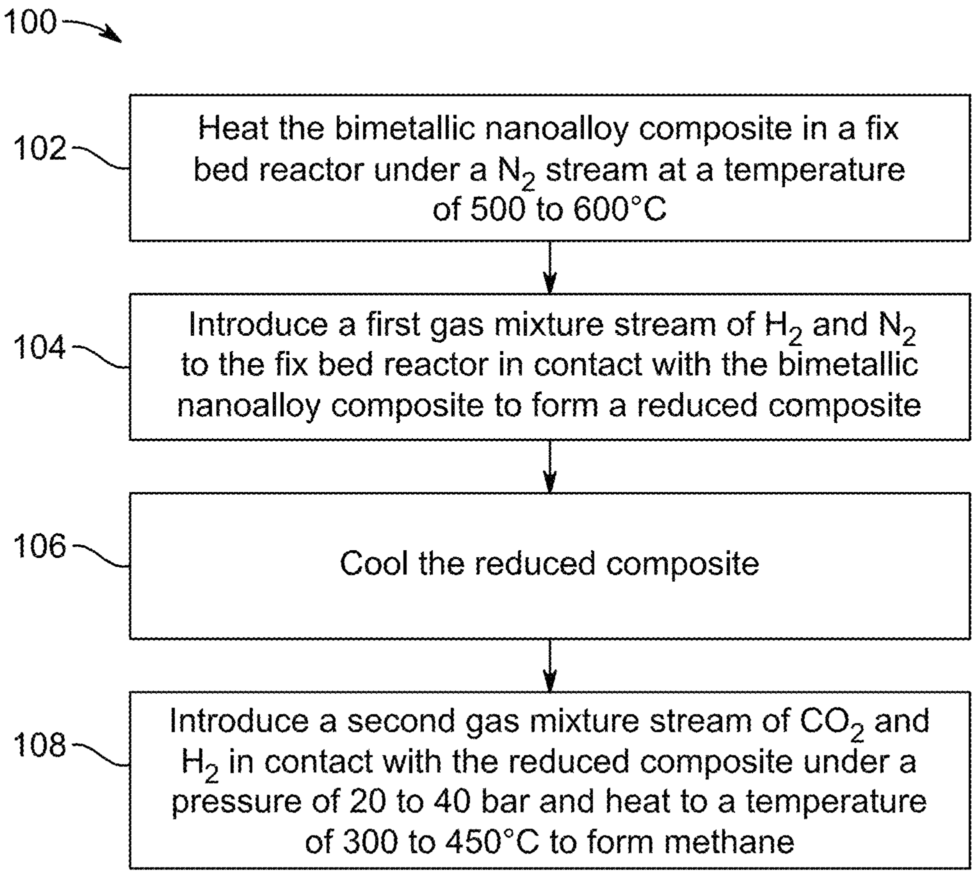
FIG. 1B is a flowchart depicting a method of making methane, according to certain embodiments.

Referring to FIG. 1B, a schematic flow diagram of the method 100 of method of making methane is illustrated. The order in which the method 100 is described is not intended to be construed as a limitation, and any number of the described method steps may be combined in any order to implement the method 100. Additionally, individual steps may be removed or skipped from the method 100 without departing from the spirit and scope of the present disclosure.

At step 102, the method 100 includes heating the bimetallic nanoalloy composite in a fix-bed reactor under a $N_2$ stream at a temperature of 500 to 600° C. In an embodiment, the method includes heating the bimetallic nanoalloy composite in the fix bed reactor under the $N_2$ stream at a temperature of 500, preferably 520, preferably 530, preferably 540, preferably 550 to about 600° C.

In a specific embodiment, the fix bed reactor is in the form of a vertical cylindrical reactor including a top portion; a vertically oriented cylindrical body portion; a bottom portion; and a housing having an open top and open bottom supportably maintained with the vertically oriented cylindrical body portion. The bimetallic nanoalloy composite is supportably retained within the housing permitting fluid flow therethrough; at least one propeller agitator is disposed in the bottom portion of the reactor. Furthermore, the bottom portion of the reactor is cone shaped or pyramidal; and the reactor includes a plurality of recirculation tubes fluidly connects the bottom portion of the vertical cylindrical reactor with the body portion of the vertical cylindrical reaction. In some embodiments, the fix bed reactor of the present method of making methane is preferably a PID/Particulate Systems Effi Microreactor. In some other embodiments, the reactor is an isothermal fix bed reactor, while in some specific embodiments, the reactor is preferably an adiabatic fix bed reactor. In yet another embodiment, the reactor is a multitubular fix bed reactor with the plurality of recirculation tubes fluidly connecting the bottom portion of the reactor.

At step 104, the method 100 includes introducing a first gas mixture stream of $H_2$ and $N_2$ to the fix bed reactor in contact with the bimetallic nanoalloy composite to form a reduced composite. In an embodiment, the flow rate ratio of the $H_2$ and the $N_2$ in the first gas mixture stream is in a range of 1:2 to 1:20, preferably 1:5 to 1:17, preferably 1:8 to 1:14, or even more preferably about 1:10. Other ranges are also possible.

At step 106, the method 100 includes cooling the reduced composite. In an embodiment, the reduced composite is cooled down to 50, preferably 60, preferably 70 to about 80° C. before being subjected to pressure and heating to form the methane. In another embodiment, the reduced composite is cooled down to about 70° C. before being subjected to pressure and heating to form the methane.

At step 108, the method 100 includes introducing a second gas mixture stream of $CO_2$ and $H_2$ in contact with the reduced composite under a pressure of 20 to 40 bar, preferably 25 to 35 bar, or even more preferably about 30 bar; and heating to a temperature of 300 to 450° C., preferably 325 to 425° C., preferably 350 to 400° C., or even more preferably about 375° C. to form the methane. In a preferred embodiment, the reduced composite is subjected to a pressure of about 30 bar followed by heating to a temperature in a range of 375° C. to form the methane. In a more preferred embodiment, the flow rate ratio of the $CO_2$ and the $H_2$ in the second gas mixture stream in a range of 10:1 to 1:1, preferably 8:1 to 2:1, preferably 6:1 to 3:1, or even more preferably 5:1 to 4:1. Other ranges are also possible.

EXAMPLES

The following examples demonstrate a method of making a bimetallic compound, and its applicability in converting $CO_2$ to methane, as described herein. The examples are provided solely for illustration and are not to be construed as limitations of the present disclosure, as many variations thereof are possible without departing from the spirit and scope of the present disclosure.

Example 1: Materials

Chemicals used for preparing the products by the methods of the present invention include Trimesic acid (98% purity) (TPA), Nickel nitrate hexahydrate (99.99% purity) ($Ni(NO_3)_2{\cdot}6H_2O$), Cobalt nitrate hexahydrate (99.99% purity) ($Co(NO_3)_2{\cdot}6H_2O$) methanol (99.9% purity), N, N-dimethylformamide (DMF; 99.8% purity), Acetic acid ($CH_3COOH$) (99.0%) dichloromethane (99.8% extra dry grade), o-Phenylenediamine (99.5%) with all the other derivatives of the aromatic diamines purchased from Sigma Aldrich Corporation. NMR solvents: dimethyl sulfoxide-d6 (DMSO-d6; 99.9% purity) were purchased from Cambridge Isotope. All chemicals were used without further purification. Water used in the experiments and demonstrations of the present invention was double distilled and filtered through a Millipore membrane.

Example 2: Instrumentation $^1H$ and $^{13}C$ NMR spectra were recorded on a Bruker AM-400 spectrometer (manufactured by Bruker Biospin Corporation, 40 Manning Rd Billerica, MA. United States) using TMS as the internal standard. Powder X-ray diffraction (PXRD) patterns of the samples were recorded using a Rigaku MiniFlex diffractometer equipped with Cu-Kα radiation (manufactured by Rigaku, 3 Chome-9-12 Matsubaracho, Akishima, Tokyo 196-8666, Japan). The data were acquired over the 2θ range of 5° and 40°. The FT-IR spectrum of the MOF was obtained using a Nicolet 6700 Thermo Scientific instrument in the range of 400-4000 $cm^{-1}$, using KBr (manufactured by Thermo Scientific, 168 Third Avenue. Waltham, MA USA 02451). Thermogravimetric analysis (TGA) was conducted using a TA Q500 with the sample held in an alumina pan under airflow (manufactured by TA instruments, 159 Lukens Drive, New Castle, DE 19720, USA). The surface area was obtained from the nitrogen adsorption isotherm of the MOF by using Micromeritics ASAP 2020 instrument (manufactured by Micrometric Instrument Corporation, 4356 Communications Dr, Norcross, GA 30093, United States). A liquid nitrogen bath was used for the measurements at 77 K. The surface morphology of these materials was discerned using a field emission scanning electron microscope (FESEM, LYRA 3 Dual Beam, Tescan, Libušina tř. 21 623 00 Brno—Kohoutovice Czech Republic), which operated at 30 kV. The FESEM samples were prepared from suspension in ethanol. The surface chemical analyses were performed using an XPS equipped with an Al-Kα micro-focusing X-ray monochromator (ESCALAB 250Xi XPS Microprobe, Thermo Scientific, 168 Third Avenue. Waltham, MA USA 02451). Inductively Coupled Plasma Mass Spectrometry (ICP-MS) of the cobalt and nickel treated samples of CoNi@C were carried out in Thermo Scientific XSeries 2 ICP-MS (manufactured by Thermo Scientific, 168 Third Avenue. Waltham, MA USA 02451). The catalysis for the benzimidazole formation was carried out in a Micro Batch Reactor System (PARR). Temperature-programmed reduction (TPR) and Temperature programmed desorption of $CO_2$ molecules ($CO_2$-TPD) were conducted using BELCAT II (MicrotracBel) analyzer (manufactured by MicrotracBel, 8-2-52 Nanko-Higashi, Suminoe-ku; Osaka, 559-0031; Japan). For $H_2$-TPR analysis, 50 mg of the catalyst was loaded and preheated under argon flow (50 ml/min) at 500° C. for 30 minutes. The sample was cooled down to 40° C. After that, a mixture of hydrogen and argon (10% $H_2$ in Ar, 50 ml/min) was passed over the catalyst, and the samples were heated to 900° C. with a ramping rate of 10° C./min. The thermal conductivity detector (TCD) signal was recorded simultaneously to determine the reducibility of the sample. For $CO_2$-TPD, the reduced sample was flushed with helium at 500° C. for 30 min. The sample was cooled down to room temperature. $CO_2$ gas was passed over the reduced sample at room temperature for 30 min (50 ml/min). After that, the sample was flushed with 50 ml/min of helium to remove the excess $CO_2$ for 30 min. Finally, the desorption of $CO_2$ was detected by the TCD detector during heating from room temperature to 800° C. with a ramping rate of 10° C./min.

Example 3: Synthesis of CoBTC

The synthesis procedure was followed as specified in the literature [Sankar, M.; Dimitratos, N.; Miedziak, P. J.; Wells, P. P.; Kiely, C. J.; Hutchings, G. J. Designing bimetallic catalysts for a green and sustainable future. Chem. Soc. Rev. 2012, 41, 8099-8139, which is incorporated herein by reference in its entirety].

Example 4: Synthesis of NiBTC

The synthesis procedure was followed as specified in the literature [Yaghi, O. M.; Li, H.; Groy, T. L. Construction of Porous Solids from Hydrogen-Bonded Metal Complexes of 1,3,5-Benzenetricarboxylic acid. J. Am. Chem. Soc. 1996, 118, 9096-9101, which is incorporated herein by reference in its entirety].

Example 5: Synthesis of CoNiBTC

CoNiBTC was synthesized by dissolving $Ni(NO_3)_2 \cdot 6H_2O$ (146 mg, 0.5 mmol), $Co(NO_3)_2$ (146 mg, 0.5 mmol), and Trimesic acid (210 mg, 1.0 mmol) in DMF (20 mL) with ultrasonic vibration for 15 min, then 5 mL of acetic acid was added. The as-obtained mixture was transferred to a 40 mL Parr steel autoclave and heated at 448 K for 72 hours. Then the autoclave was cooled in the air to room temperature. The resulting microcrystalline powder was collected and washed with 3×10 mL of DMF for three days and 3×10 mL of $CH_2Cl_2$ for three days yielding the required CoNiBTC in 55% yield (related to the metal salt).

FT-IR (KBr, $cm^{-1}$): 3418, 1668, 1608, 1561, 1442, 1429, 1102, 769, 710, 674.

Example 6: Synthesis of CoNiBTC-1

The synthesis method was identical to that of CoNiBTC. $Ni(NO_3)_2 \cdot 6H_2O$ (146 mg, 0.5 mmol), $Co(NO_3)_2$ (98 mg, 0.33 mmol), and trimesic acid (210 mg, 1.0 mmol) in DMF (20 mL) with ultrasonic vibration for 15 min, then 5 mL of acetic acid was added. The obtained mixture was transferred to a 40 mL Parr steel autoclave and heated at 448 K for 72 h.

Example 7: Synthesis of CoNiBTC-2

The synthesis method was identical to that of CoNiBTC. $Ni(NO_3)_2 \cdot 6H_2O$ (219 mg, 0.75 mmol), $Co(NO_3)_2$ (98 mg, 0.33 mmol), and trimesic acid (210 mg, 1.0 mmol) in DMF (20 mL) with ultrasonic vibration for 15 min, then 5 mL of acetic acid was added. The as-obtained mixture was transferred to a 40 mL Parr steel autoclave and heated at 448 K for 72 h.

Example 8: Synthesis of CoNi@C

The synthesized CoNiBTC (500 mg) as depicted in aforementioned Example 5, was carbonized to produce CoNi@C. The pyrolysis process was performed in a quartz tubular reactor by loading the catalyst in the reactor tube. The sample was heated to 750° C. using nitrogen (25 ml/min) at a ramping rate of 5° C./min, then held at that temperature for 8.0 hours. The sample was then cooled to room temperature before being exposed to 5 ml/min of oxygen and 25 ml/min of nitrogen for two hours.

Example 9: Synthesis of CoNi@C-1

The synthesized CoNiBTC-1 (500 mg) as depicted in aforementioned Example 6, was carbonized to produce CoNi@C-1. The pyrolysis process was performed in a quartz tubular reactor by loading the catalyst in the reactor tube. The sample was heated to 750° C. using nitrogen (25 ml/min) at a ramping rate of 5° C./min, then held at that temperature for 8.0 hours. The sample was then cooled to room temperature before being exposed to 5 ml/min of oxygen and 25 ml/min of nitrogen for two hours to afford the CoNi@C-1.

Example 10: Synthesis of CoNi@C-2

The synthesized CoNiBTC-2 (500 mg) as depicted in aforementioned Example 7, was carbonized to produce CoNi@C-2. The pyrolysis process was performed in a quartz tubular reactor by loading the catalyst in the reactor tube. The sample was heated to 750° C. using nitrogen (25 ml/min) at a ramping rate of 5° C./min, then held at that temperature for 8.0 hours. The sample was then cooled to room temperature before being exposed to 5 ml/min of oxygen and 25 ml/min of nitrogen for two hours to afford the CoNi@C-2.

Example 11: Synthesis of Co@C

The synthesized CoBTC (500 mg) as depicted in aforementioned Example 3, was carbonized to produce Co@C. The pyrolysis process was performed in a quartz tubular reactor by loading the catalyst in the reactor tube. The sample was heated to 750° C. using nitrogen (25 ml/min) at a ramping rate of 5° C./min, then held at that temperature for 8.0 hours. The sample was then cooled to room temperature before being exposed to 5 ml/min of oxygen and 25 ml/min of nitrogen for two hours to afford the Co@C.

Example 12: Synthesis of Ni@C

The synthesized NiBTC (500 mg) as depicted in aforementioned Example 4, was carbonized to produce Ni@C. The pyrolysis process was performed in a quartz tubular reactor by loading the catalyst in the reactor tube. The sample was heated to 750° C. using nitrogen (25 ml/min) at a ramping rate of 5° C./min, then held at that temperature for 8.0 hours. The sample was then cooled to room temperature before being exposed to 5 ml/min of oxygen and 25 ml/min of nitrogen for two hours to afford the Ni@C.

Example 13: Catalysis of Benzimidazole Synthesis

The cyclization reaction of ortho-substituted aniline with $CO_2/H_2$ was performed in a 10 mL high-pressure Micro Batch Reactor System (PARR) coupled with a magnetic stirrer. Typically, ortho-substituted aniline (1 mmol), CoNi@C (100 mg), and ethanol (5 mL) were loaded into the reactor. The autoclave was closed and then charged with $CO_2$ to 15 bar, further with $H_2$ up to a total pressure of 30 bar at room temperature. Subsequently, the reactor was heated at 115° C. with stirring. After 18-hours the reactor was cooled down, and the gas inside was carefully vented. The crude reaction mixture was centrifuged with ethyl acetate to separate the catalyst and then concentrated using a rotary evaporator and purified by column chromatography using ethyl acetate/dichloromethane to give the isolated compound that was characterized by $^1$H NMR, and $^{13}$C NMR.

Example 14: Catalysis of $CO_2$ Methanation

The methanation process of $CO_2$ was performed using a fixed bed reactor (PID Microactivity-Effi reactor) at 375° C. and 30 bar. An Inconel reactor tube with an internal diameter of 8 mm was used to carry on the reaction. The catalyst sample (200 mg) was pelletized in a pellet size of 100-300 microns and then loaded in between two layers of quartz wool inside the reactor tube. The sample was preheated with the ramping rate of 15° C./min to 550° C. under a continuous flow of $N_2$ gas (20 ml/min) for 30 min. After that, the sample was reduced under $H_2$ (3 ml/min) and $N_2$ (20 ml/min) flow for another 30 min. After the reduction, the sample was cooled down to 70° C. and then pressurized with the reactant feed to 30 bar and then heated to reaction temperature (375° C.) to carry on the reaction. The reactant feed was a mixture of $CO_2$ and $H_2$ with an $H_2$ to $CO_2$ ratio of 3, and the feed flow rate was kept at 15 ml/min with gas hourly space velocity (GHSV) of 4500 ml/(g·h$^{-1}$). The quantitative and qualitative analysis was performed using gas chromatography (Shimadzu, GC-2014, manufactured by Shimadzu Corporation, 1, Nishinokyo Kuwabara-cho, Nakagyo-ku, Kyoto 604-8511, Japan) equipped with one TCD and one flammable ionization detector (FTD).

Example 15: Results

Figure 4A:
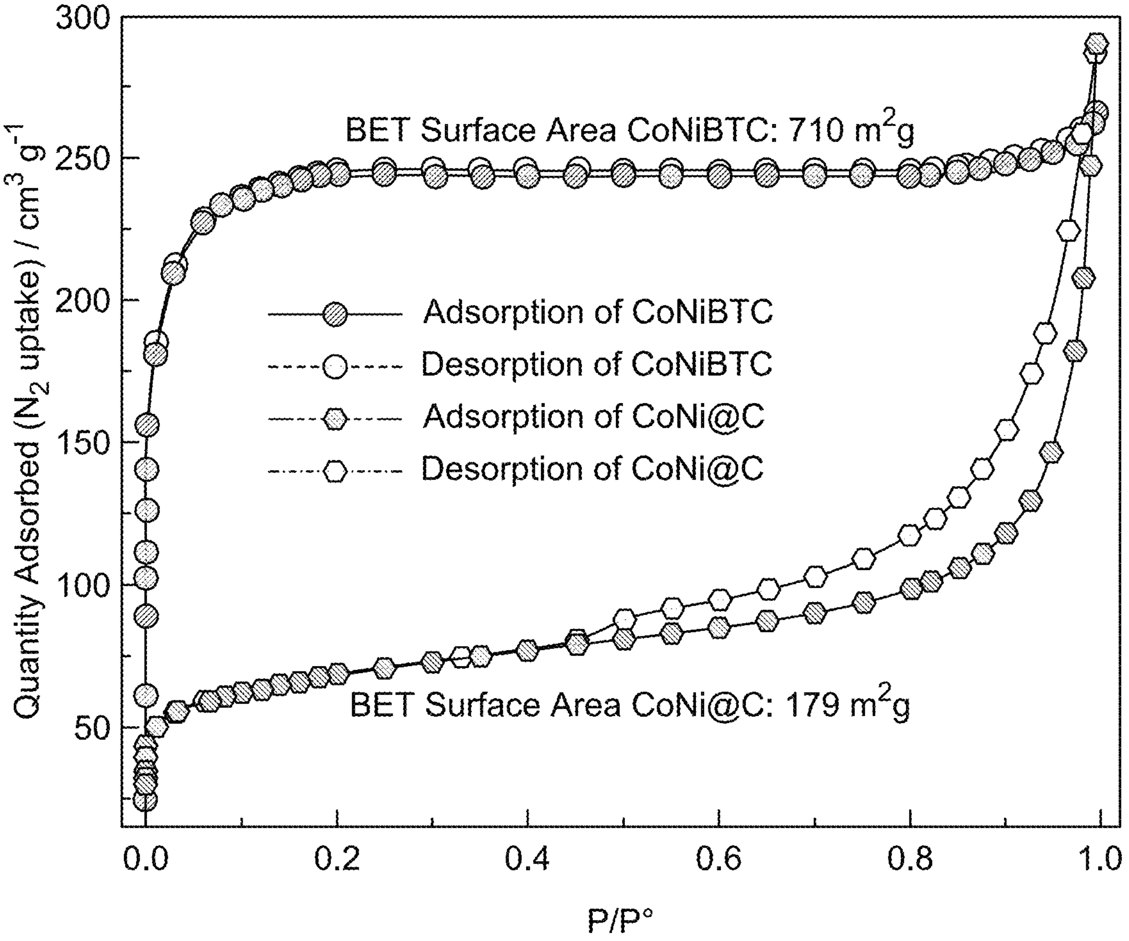
FIG. 4A shows a $N_2$ adsorption isotherm of CoNiBTC and CoNi@C; according to certain embodiments.
Figure 4B:
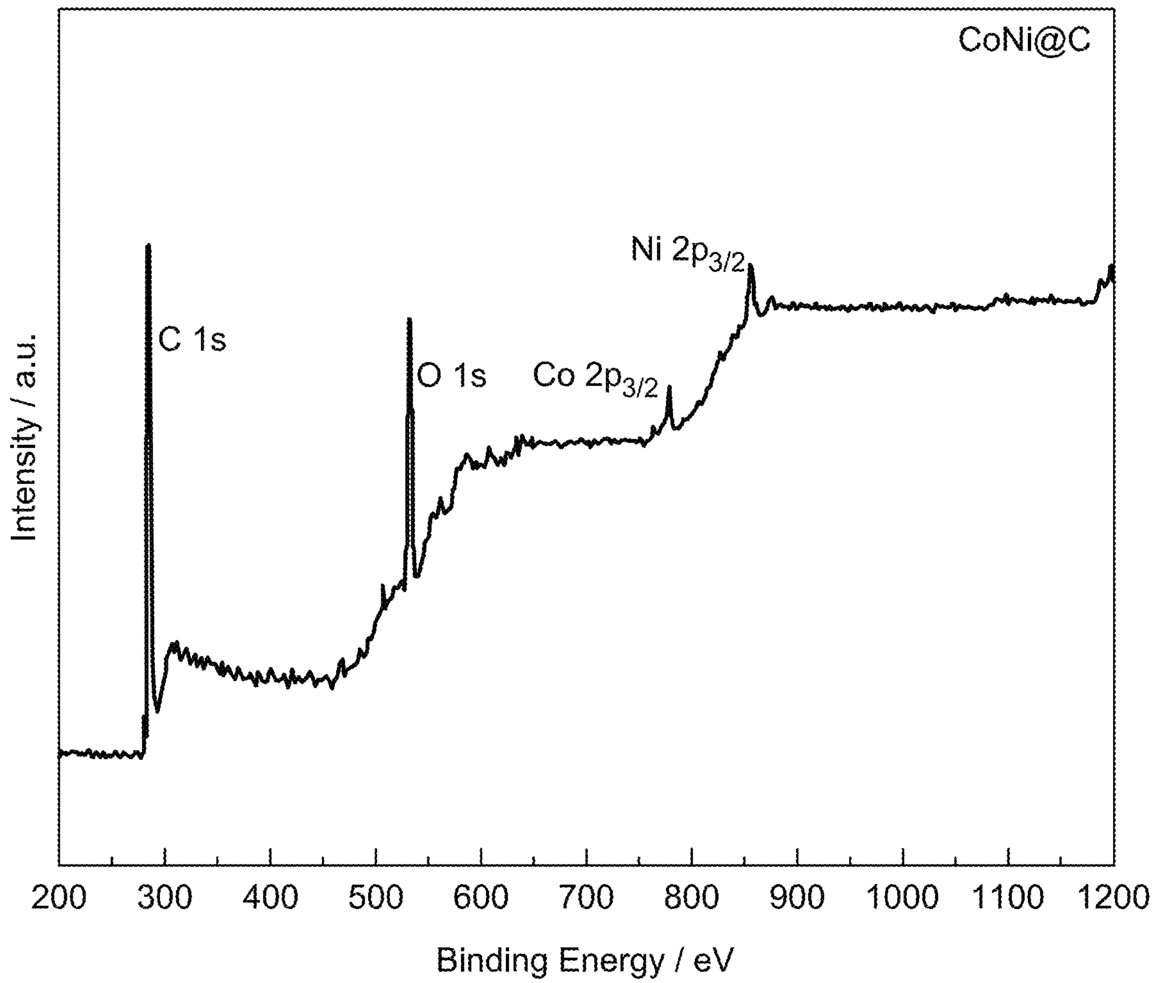
FIG. 4B shows an X-ray photoelectron spectroscopy (XPS) spectrum of CoNi@C; according to certain embodiments.
Figure 5:
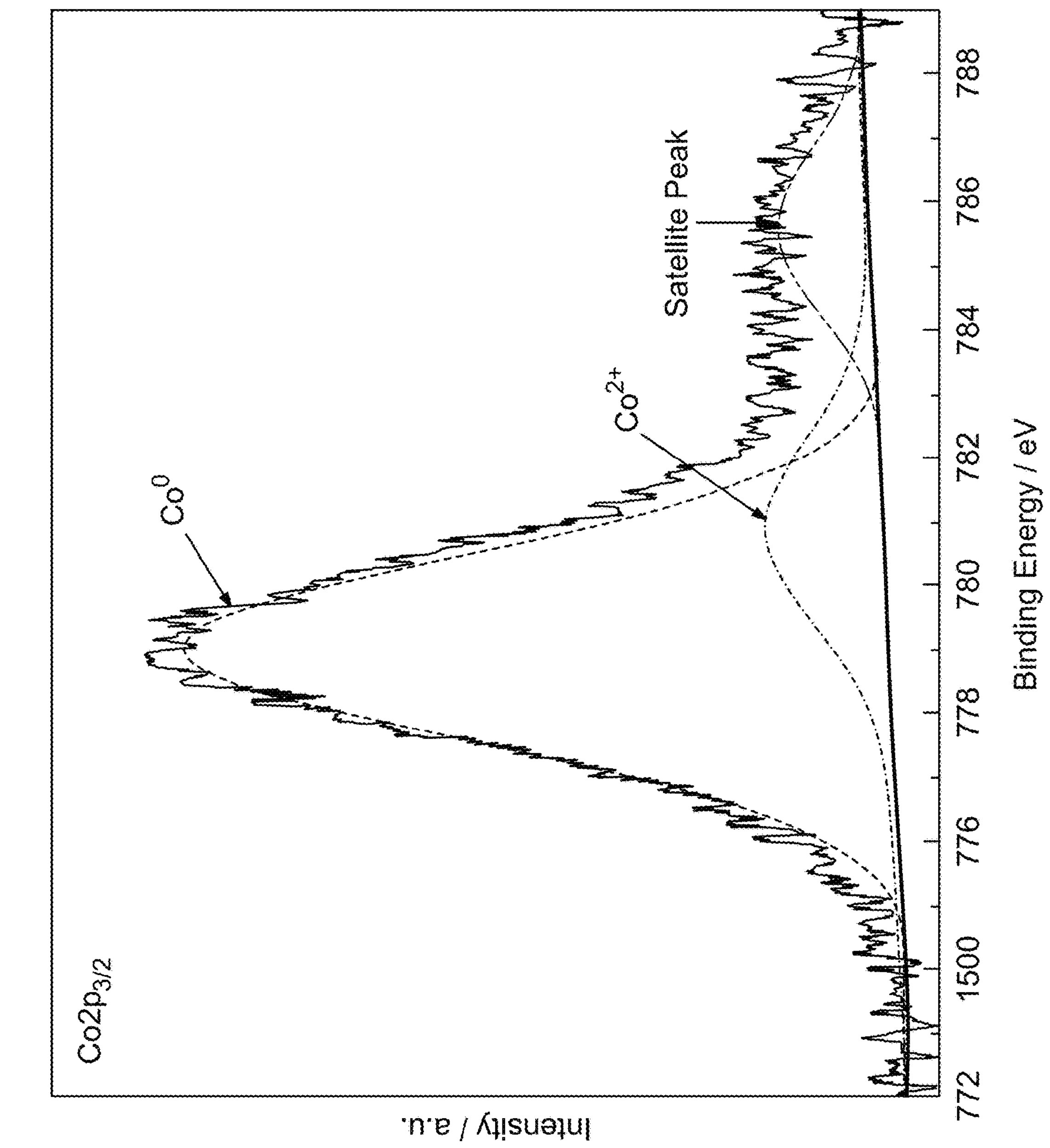
FIG. 5 shows a deconvoluted XPS spectrum of Co 2p3/2; according to certain embodiments.
Figure 6:
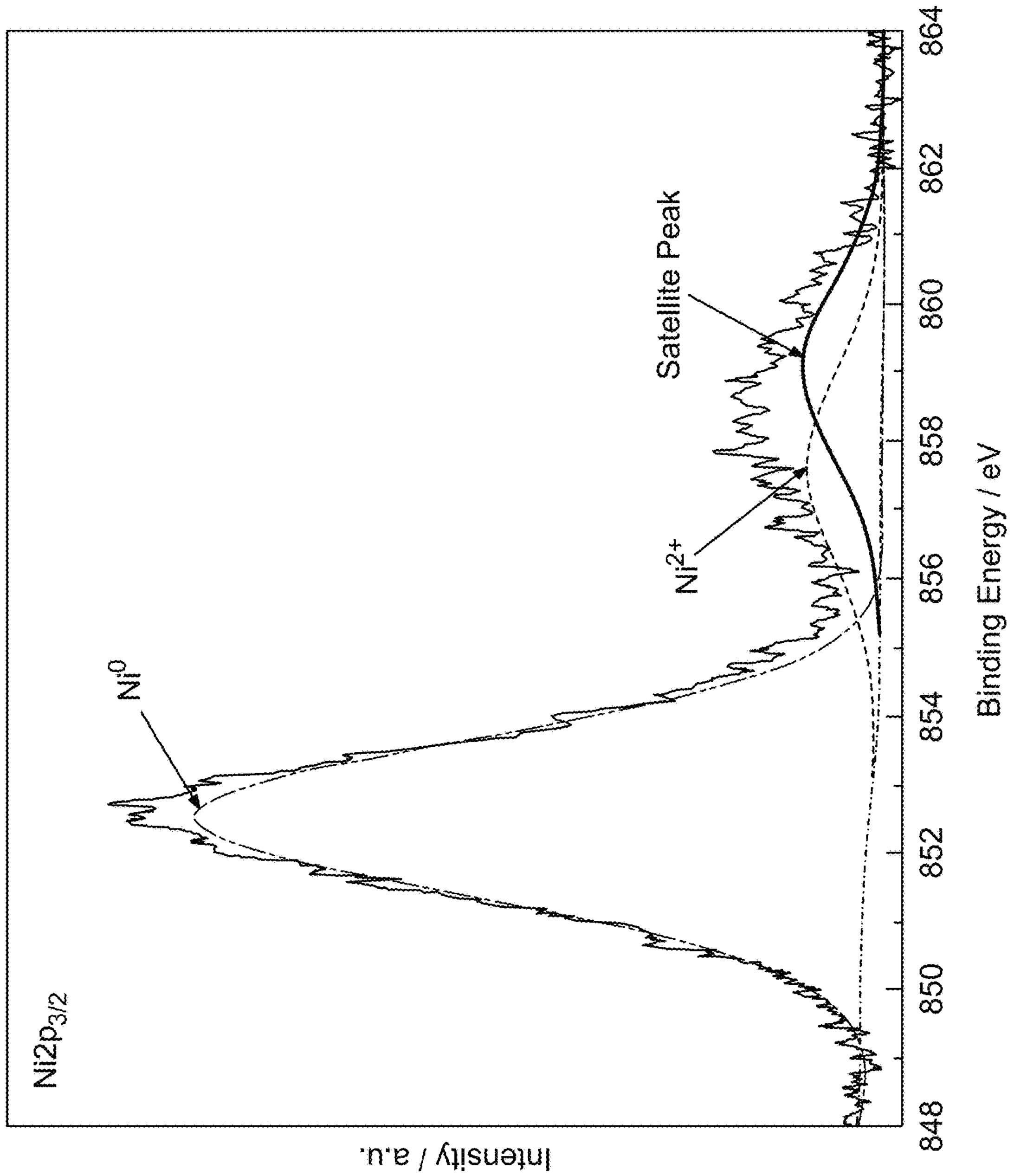
FIG. 6 shows a deconvoluted XPS spectrum of Ni 2p3/2; according to certain embodiments.

Referring now to FIG. 2, the synthesis of bimetallic CoNiBTC precursor was carried out following a slightly modified method as mentioned in the literature for the synthesis of CoBTC MOF [He, J.; Zhang, Y.; Pan, Q.; Yu, J.; Xu, R. Microporous Mesoporous Mater. 2006, 90, 145-152, which is incorporated herein by reference in its entirety]. An equimolar ratio of cobalt nitrate and nickel nitrate was dissolved with trimesic acid in dimethylformamide as the solvent and acetic acid as a modulator and heated at 448 K for 72 h. Similarly, by varying the ratio of cobalt nitrate and nickel nitrate, CoNiBTC-1 and CoNiBTC-2 were prepared. Similarly, CoBTC and NiBTC were synthesized using the standard procedure. The MOFs obtained were washed by solvent exchange and utilized as a precursor for the design and synthesis of MOF-derived porous CoNi@C, CoNi@C-1, CoNi@C-2, Co@C, and Ni@C composites with well-dispersed Co and Ni nanoparticles enclosed in carbon shells. The PXRD of the CoBTC, NiBTC, and CoNiBTC exhibited that all the MOFs are crystalline, and the topologies are the same as the simulated CoBTC known in the art with characteristic peaks at 2θ=7.55°, 11.02°, and 12.81° [Bavykina, A.; Kolobov, N.; Khan, I. S.; Bau, J. A.; Ramirez, A.; Gascon, G. Metal-Organic Frameworks in Heterogeneous Catalysis: Recent Progress, New Trends, and Future Perspectives. Chem. Rev. 2020, 120, 8468-8535, which is incorporated herein by reference in its entirety]. The CoNiBTC-1 and CoNiBTC-2 exhibit similar distinctive peaks as well (FIG. 2C). This signifies that the presence of nickel in the CoNiBTC does not disturb the topology or the phase purity of the CoBTC MOF (FIG. 2A). After pyrolysis, Co@C, Ni@C, and CoNi@C also displayed good crystallinity with the characteristic peaks for graphite (2θ=30.60) and cubic phase of metallic Co, Ni, and Ni—Co ([111] [200] [220] facets) 2θ=44.4°, 51.77° and 76.16° (FIG. 2B and FIG. 2D). The inductively coupled plasma mass spectroscopy (ICP-MS) analysis of CoNiBTC revealed that the amounts of Co and Ni were 17% and 11%, respectively, while the amounts of metals in the CoNi@C were 35% and 23%. The bands at 710 cm$^{-1}$ and 769 cm$^{-1}$ in the Fourier Transform Infra-Red spectroscopy (FTIR) spectrum of CoNiBTC, as illustrated in FIG. 3 correspond to the linker's out-of-plane aromatic C—H bending modes. The peak at 1102 cm$^{-1}$ is due to aromatic C—H in-plane bending, whereas the sharp peaks (1429, 1442 cm$^{-1}$) and (1561, 1608 cm$^{-1}$) are due to the COO— group's symmetric and asymmetric C—O stretching modes. The $N_2$ adsorption isotherm of the precursor CoNiBTC MOF displayed a sharp uptake at low pressure indicating a type I isotherm with a completely microporous nature. The BET surface area was calculated to be 710 m$^2$g$^{-1}$. However, the $N_2$ adsorption isotherm of CoNi@C after pyrolysis showed a hysteresis loop within the $P/P_o$ range of 0.7-1 due to the material's micro-mesoporous nature. The surface area of CoNi@C was calculated to be 179 m$^2$/g. The massive decrease in surface area is due to the annihilation of the MOF framework and a decrease in microporosity (FIG. 4A). Referring to FIG. 4B, an XPS spectrum of CoNi@C is depicted. The main characteristic peaks with binding energies for the metals were Co 2p$^{3/2}$ at 778.8 eV (Co$^0$) and Ni 2p$^{3/2}$ at 852.8 eV (Ni$^0$), confirming the presence of the two metals in CoNi@C. The deconvoluted Co 2p$^{3/2}$ data revealed three notable peaks at 778.8, 780.8, and 785.7 eV, which were indexed as Co$^0$, the major peak, Co—O, and the satellite peak of the Co—O, respectively, as shown in FIG. 5. Similarly, Ni 2p$^{3/2}$ peaks fitted into three different peaks at around 852.5, 857.4, and 859.0 eV due to the NiO, the major peak, $Ni^{2+}$, and the satellite peak of $Ni^{2+}$, respectively as shown in FIG. 6. In addition, a graphitic carbon peak corresponding to sp2 hybridization is detected at 284.3 eV.

$CO_2$-TPD was performed to determine the strength of surface basic sites for the bimetallic nanoalloy (CoNi@C) of Co and Ni. As depicted in FIG. 7A, CoNi@C has a broad peak between 50-300° C. indicating the existence of weak and moderate basic sites. A steep peak is also detected around 424° C. due to the presence of strong basic sites. Thus, the catalyst has three weak, moderate, and strong basic sites that enhance $CO_2$ adsorption. Temperature-programmed reduction with hydrogen was used to determine the reducibility behavior of the Co and Ni bimetallic nanoalloy (CoNi@C). The presence of Ni in the Ni—Co alloy enhances the reducibility of the Cobalt [Fakeeha, A. H.; Arafat, Y.; Ibrahim, A. A.; Shaikh, H.; Atia, H.; Abasaeed, A. E.; Armbruster, U.; Al-Fatesh, A. S. Processes 2019, 7, 141-158, which is incorporated herein by reference in its entirety]. Referring to FIG. 7B, a huge, broad peak centered at 590° C. was observed between 400-850° C., indicating mixed CoO and NiO reduction to metals leading to more reducible species.

Figure 9:
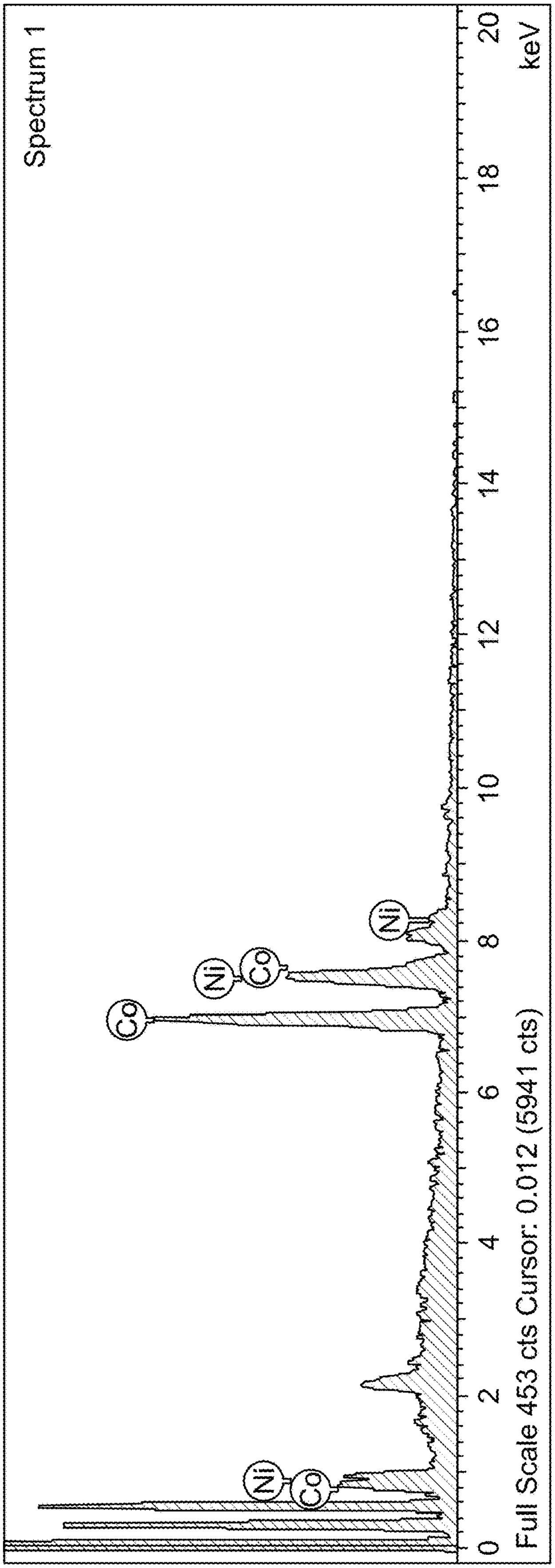
FIG. 9 shows an Energy-dispersive X-ray spectroscopy (EDX) of bimetallic CoNiBTC; according to certain embodiments.

FESEM data of the CoNiBTC showed hexagonal-shaped layered microcrystalline materials, as shown in FIG. 8. Energy-dispersive X-ray spectroscopy (EDX) and elemental mapping analysis revealed that the Co/Ni ratio in the CoNiBTC MOF was 3:2, as depicted in FIG. 9, which is in consonance with the ratio determined by the ICP-MS. The ratio of the metals in bimetallic CoNiBTC is given in Table 1.

TABLE 1

Ratio of the metals in bimetallic CoNiBTC

| Element | Weight % | Atomic % |
|---|---|---|
| Co K | 61.61 | 61.52 |
| Ni K | 38.39 | 38.48 |
| Total | 100 | 100 |

Figure 10A:
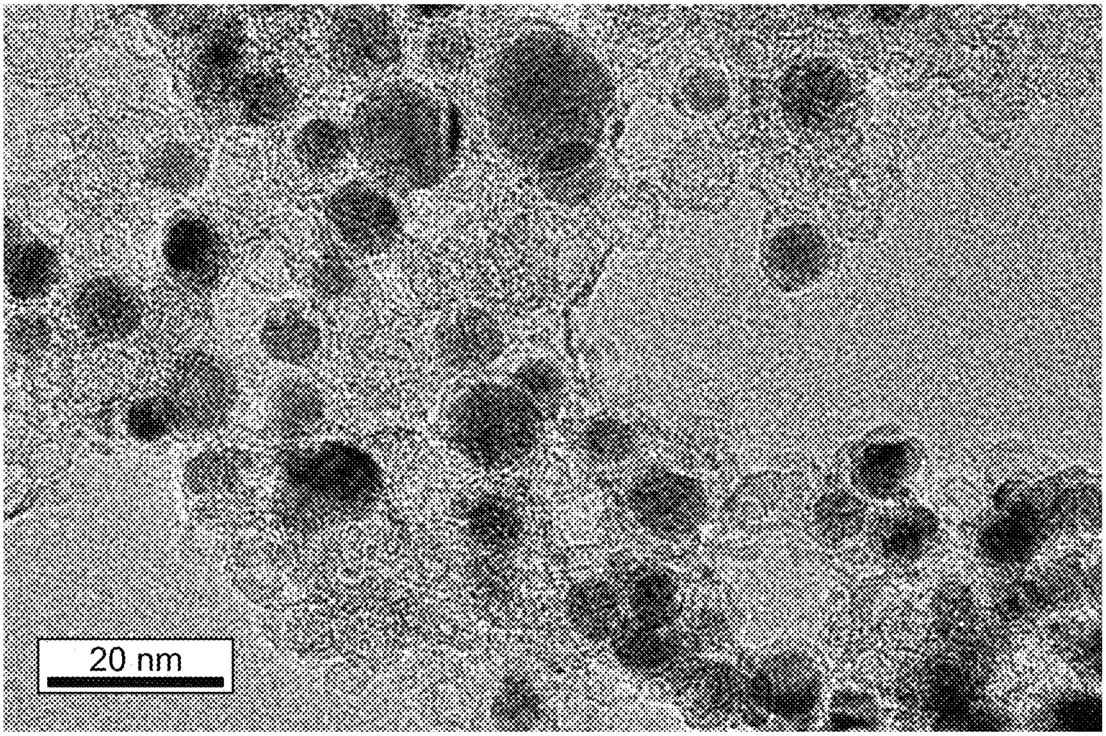
FIG. 10A shows a Transmission electron microscopy (TEM) of CoNi@C at 20 nanometers (nm); according to certain embodiments.
Figure 10B:
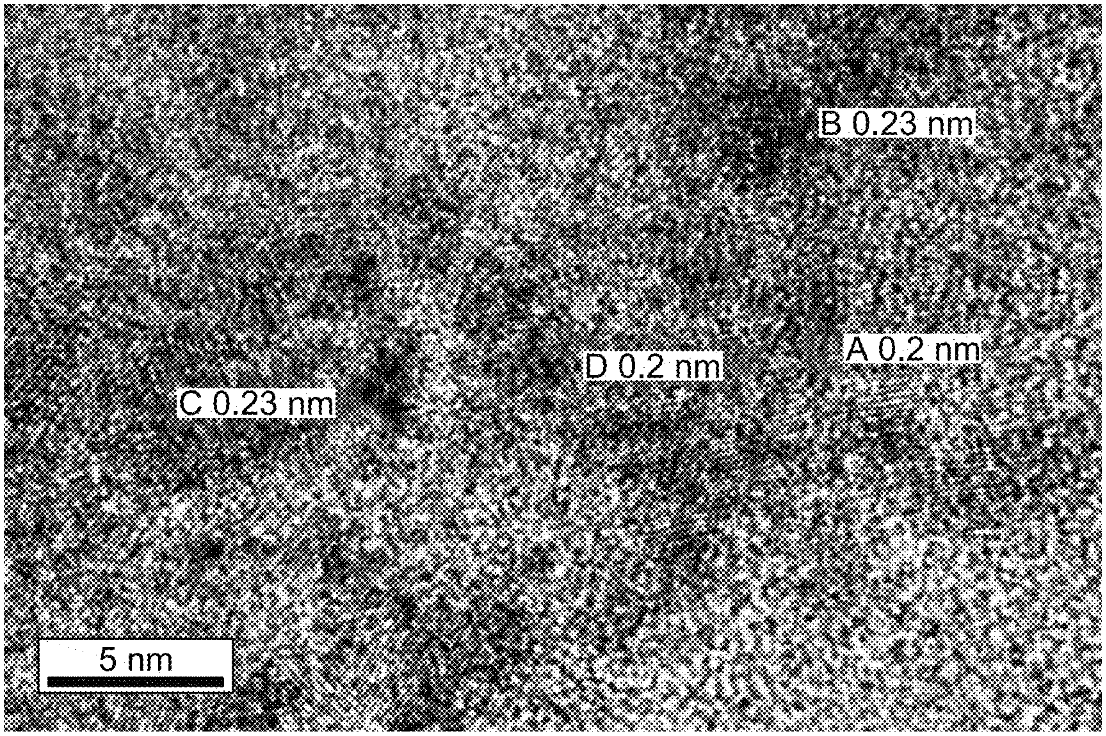
FIG. 10B shows a TEM of CoNi@C at 5 nanometers (nm); according to certain embodiments.
Figure 12:
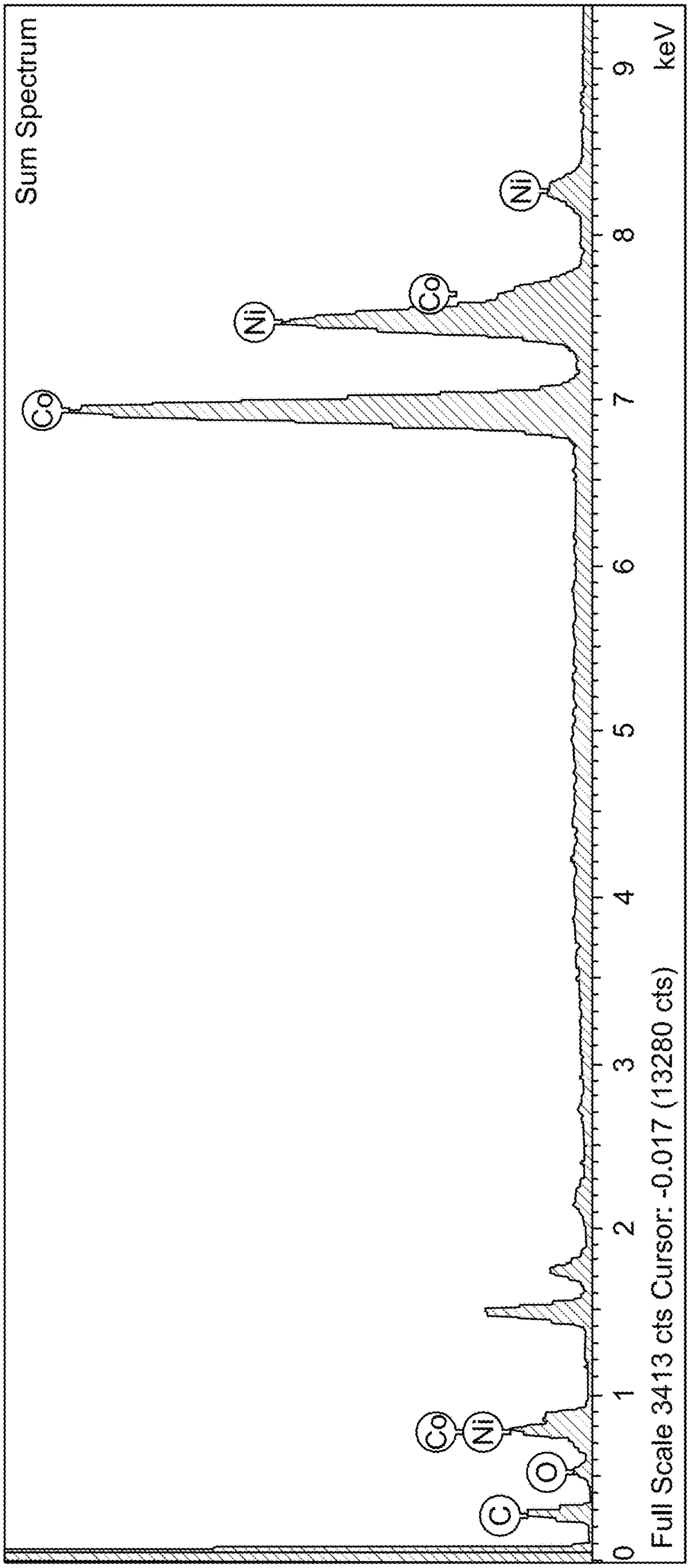
FIG. 12 shows EDX of the bimetallic CoNiBTC-1, according to certain embodiments.
Figure 14:
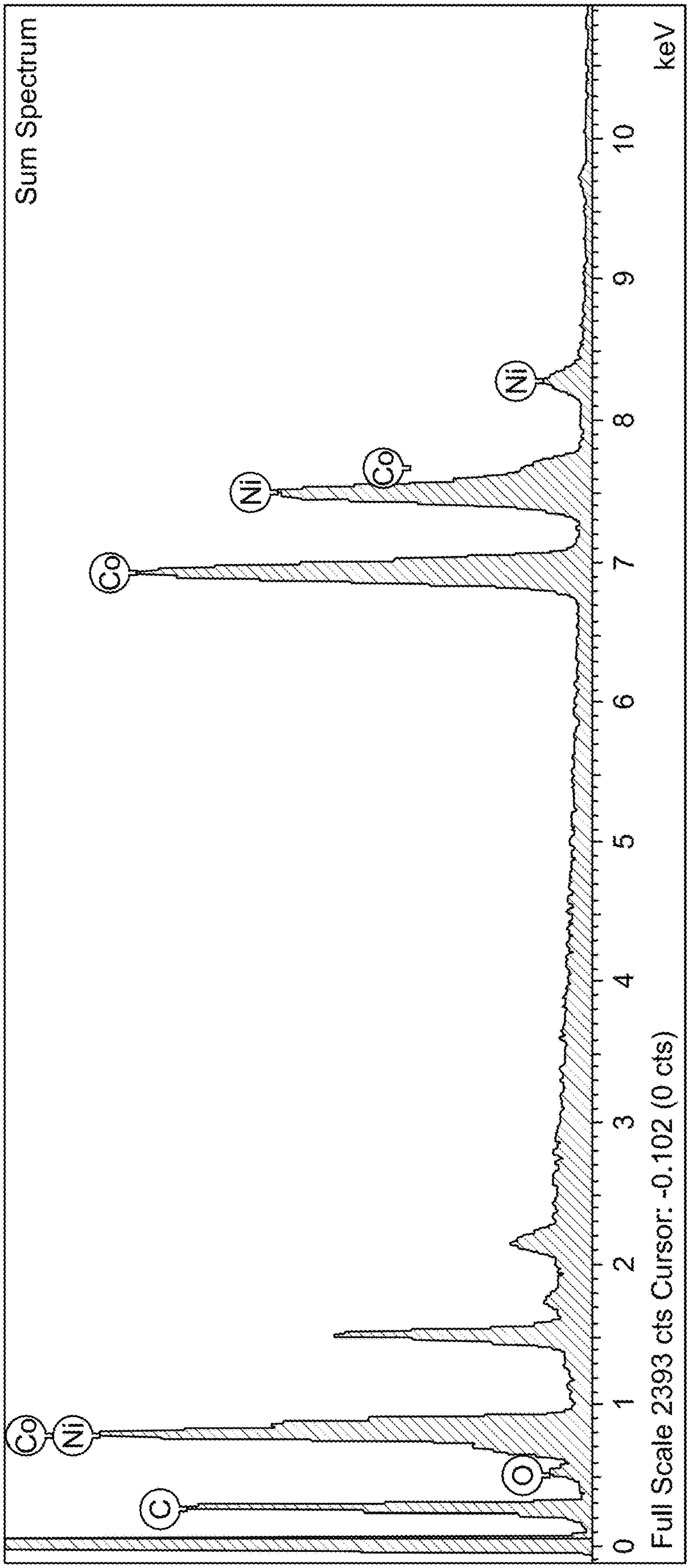
FIG. 14 shows EDX of the bimetallic CoNiBTC-2, according to certain embodiments.

TEM images of CoNi@C revealed a consistent distribution of Co—Ni nanoalloy with a size between 5 and 10 nm encased by a carbon layer. There was no discernible aggregate formation detected. Additionally, as illustrated in FIG. 10A and FIG. 10B, the particle lattice's average interplanar spacing was 0.21 nm, which is equivalent to the lattice spacing of nanoparticles made of the Co—Ni alloy [Long, J.; Shen, K.; Chen, L.; Li, Y. J. Multimetal-MOF-derived transition metal alloy NPs embedded in an N-doped carbon matrix: Highly active catalysts for hydrogenation reactions. Mater. Chem. A 2016, 4, 10254-10262, which is incorporated herein by reference in its entirety]. EDX analysis of the two bimetallic MOFs, CoNiBTC-1 and CoNiBTC-2 indicated that the Co/Ni ratio was 1:1 in CoNiBTC-1 (FIG. 11 and FIG. 12) and 2:3 in CoNiBTC-2 (FIG. 13 and FIG. 14). The ratio of metals in bimetallic CoNiBTC-1 and CoNiBTC-2 are presented in Table 2 and Table 3 respectively.

TABLE 2

Ratio of the metals in bimetallic CoNiBTC-1

| Element | Weight % | Atomic % |
|---|---|---|
| Co K | 52.18 | 52.23 |
| Ni K | 47.82 | 47.77 |
| Total | 100 | 100 |

TABLE 3

Ratio of the metals in bimetallic CoNiBTC-2

| Element | Weight % | Atomic % |
|---|---|---|
| Co K | 39.47 | 39.36 |
| Ni K | 60.53 | 60.64 |
| Total | 100 | 100 |

Thus, from these MOFs, three bimetallic nanocatalysts with varying Co/Ni ratio, including CoNi@C (3:2), CoNi@C-1(1:1) and CoNi@C-2(2:3) were prepared.

Example 16: Synthesis of Benzimidazoles

The catalytic activities of CoNi@C were evaluated, and the reaction conditions were optimized using o-phenylenediamine as the model substrate with $CO_2$ and $H_2$. A blank test was run in the absence of catalysts, and no benzimidazole was produced (Table 4, entry 1). Similarly, no benzimidazole was produced in the presence of cobalt or nickel salts as catalysts. In the presence of the pristine bimetallic MOF CoNiBTC, the conversion is very low, even at elevated temperatures (Table 4, entries 4 and 5). In addition, the conversion to benzimidazole was examined in the presence of Ni@C and Co@C, which produced poor yields at identical conditions. This proves that the bimetallic nanoalloy's synergistic impact enhances the conversion (Table 4, entries 6 and 7). Consequently, maximal yield is achieved by employing the catalyst CoNi@C (Table 4, entries 8). Additionally, the ratio of Co/Ni was altered, but the yield was less than expected (Table 4, entry 9 and 10), indicating that the ratio of CoNi@C is the most successful in the conversion to benzimidazole.

TABLE 4

Synthesis of benzimidazole with different catalysts[a]

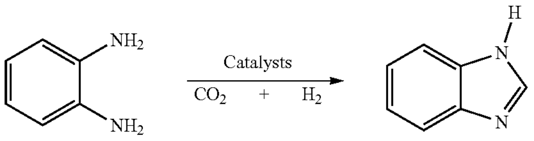

| Entry | Catalysts | Temperature/° C. | Yield/%[b] |
|---|---|---|---|
| 1 | — | 115 | 0 |
| 2 | $Ni(NO_3)_2 \cdot 6H_2O$ | 115 | 0 |
| 3 | $Co(NO_3)_2 \cdot 6H_2O$ | 115 | 0 |
| 4 | CoNiBTC | 115 | 9 |
| 5 | CoNiBTC | 130 | 11 |
| 6 | Co@C | 115 | 40 |
| 7 | Ni@C | 115 | 33 |
| 8 | CoNi@C | 115 | 81 |
| 9 | CoNi@C-1 | 115 | 52 |
| 10 | CoNi@C-2 | 115 | 38 |

[a]Reaction conditions: o-phenylenediamine, 1.0 mmol; pressure, 30 bar, time, 18 h.
[b]Isolated yield calculated from the $^1$HNMR.

Figure 15:
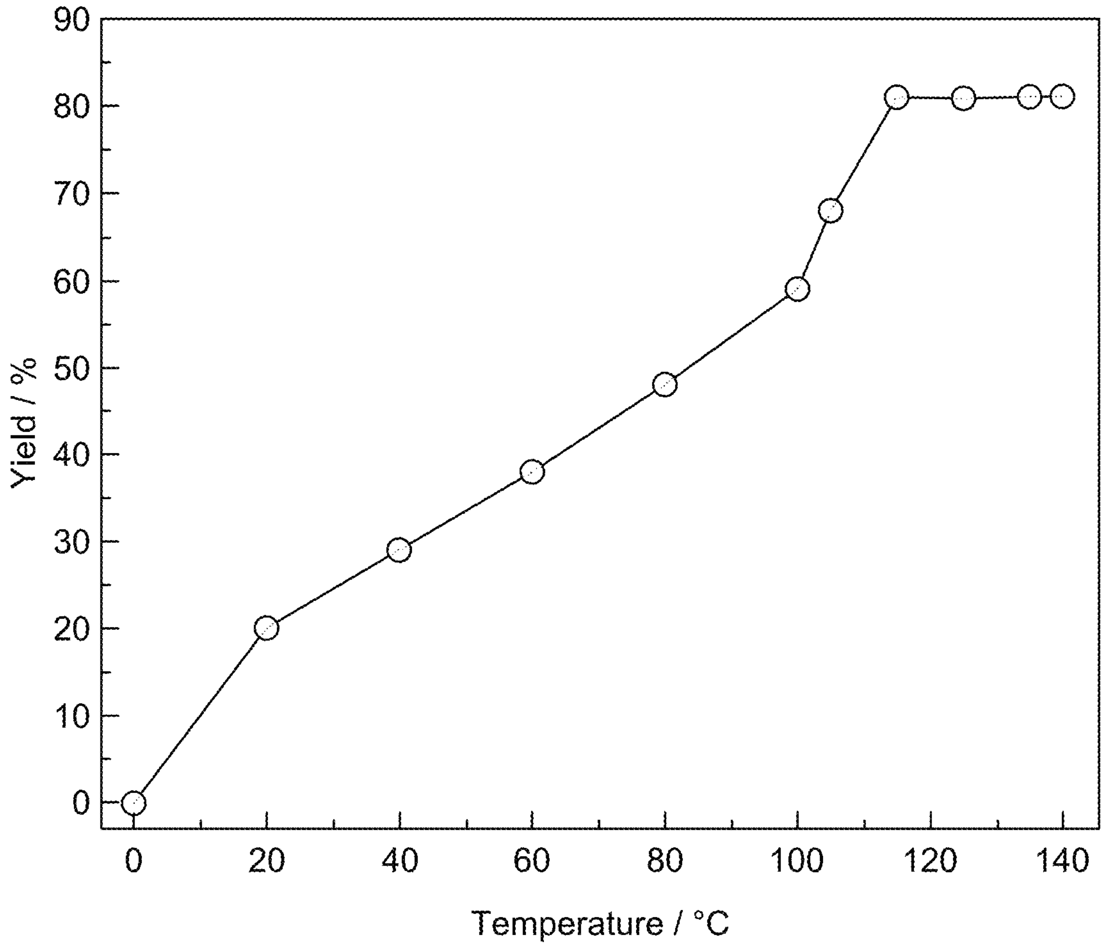
FIG. 15 illustrates a relationship between reaction temperature and benzimidazole yield; according to certain embodiments.
Figure 16:
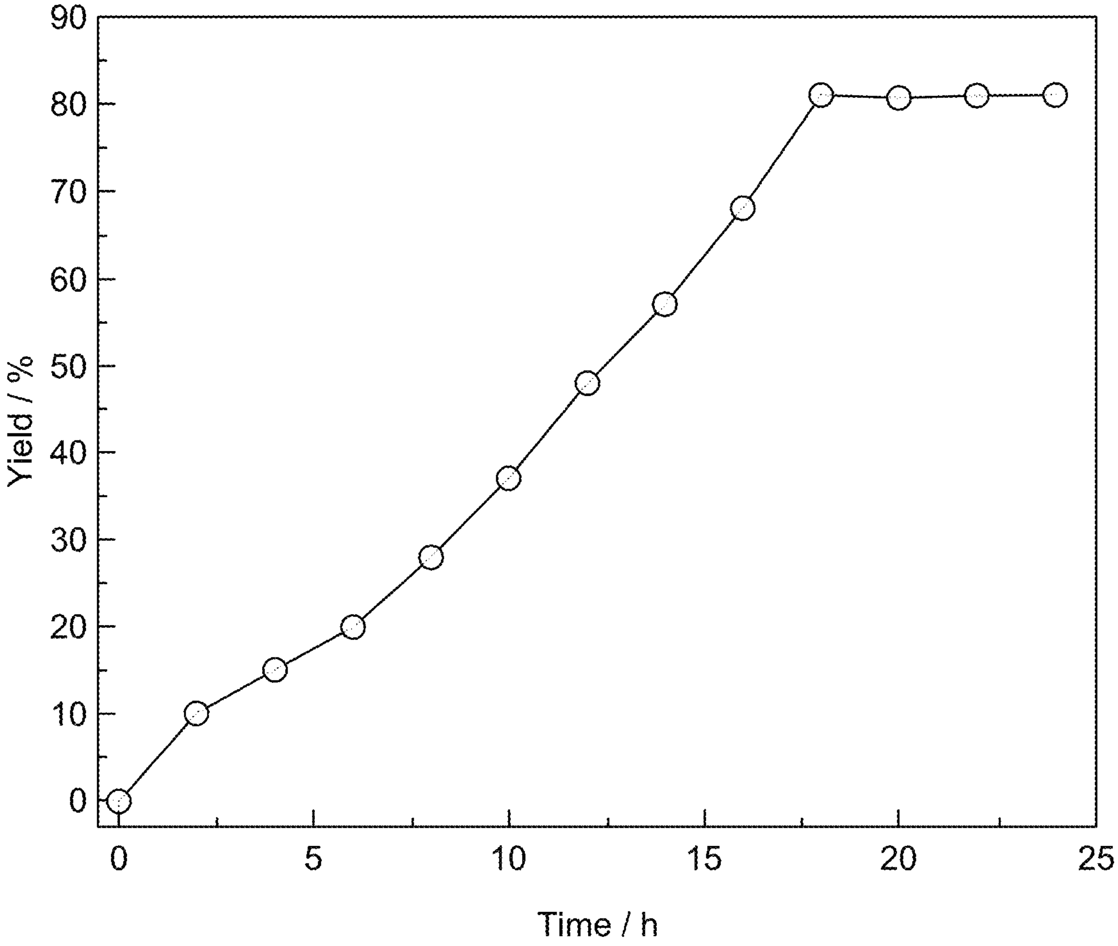
FIG. 16 illustrates an effect of reaction time on the yield of benzimidazole, according to certain embodiments.

The synthesis of benzimidazole from o-phenylenediamine was examined in depth utilizing CoNi@C as catalysts. Referring to FIG. 15, a relationship between reaction temperature and benzimidazole yield is depicted. At constant pressure and reaction time, the yield of benzimidazole increased with increasing temperature and remained constant at a specific temperature. Referring to FIG. 11B, the effect of reaction duration on benzimidazole yield was also investigated. The yield was shown to rise with a reaction time of up to 18 hours, after which the yield remained constant. Furthermore, the effect of reaction duration on benzimidazole yield was studied, and the results indicate that the yield was shown to rise with a reaction time up to 18 h, after which the yield remained constant (FIG. 16). Considering the preliminary results of benzimidazole synthesis, the general applicability and adaptability of the catalyst were further investigated in the synthesis of other substituted benzimidazoles. The cyclization of a variety of structurally different phenylenediamine with different electron-donating and electron-withdrawing functional groups by $CO_2$ in the presence of $H_2$ catalyzed by CoNi@C was also investigated. Regardless of the substituents, the corresponding substituted benzimidazole derivatives were produced in good yield (Table 5). This demonstrates conclusively that substituted groups have no effect on the cyclization of substrates by $CO_2$ in the presence of $H_2$ and CoNi@C as the catalyst. Additionally, all the products were characterized by $^1$H and $^{13}$C NMR.

Figure 17:
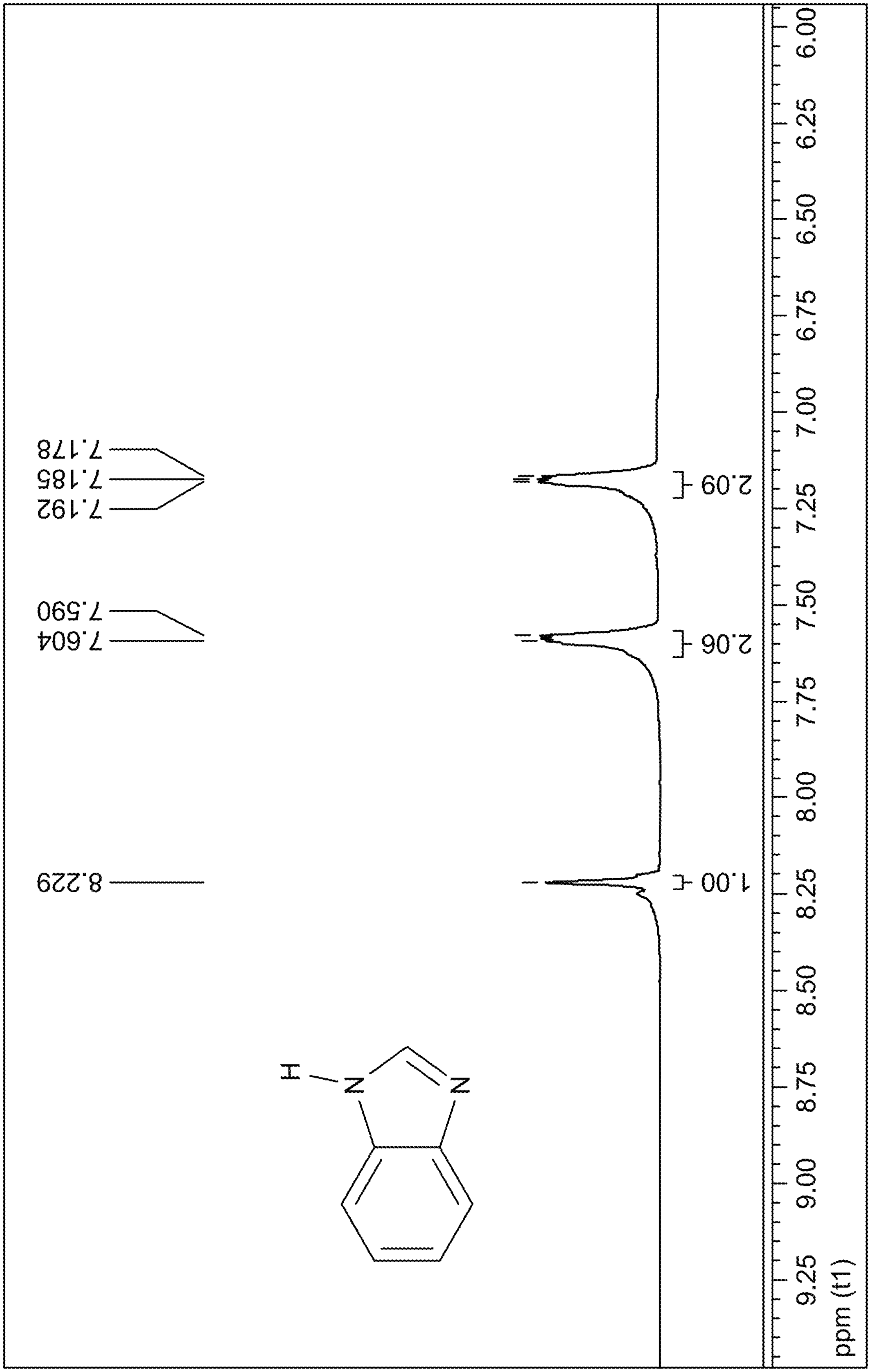
FIG. 17 shows a $^1$H nuclear magnetic resonance (NMR) spectrum 1H-benzo[d]imidazole (entry 1, Table 2), according to certain embodiments.

The $^1$H and $^{13}$C NMR of 1H-benzo[d]imidazole (entry 1, Table 5): $^1$H NMR (DMSO-d6, 400 MHz, ppm.): δ 8.23 (s, 1H), 7.59 (d, J=5.6 Hz, 2H), 7.18 (t, J=2.8 Hz, 2H) (FIG. 17); $^{13}$C NMR (DMSO-d6, 400 MHz, ppm): δ 141.9, 138.1, 121.7, 115.3.

Figure 18:
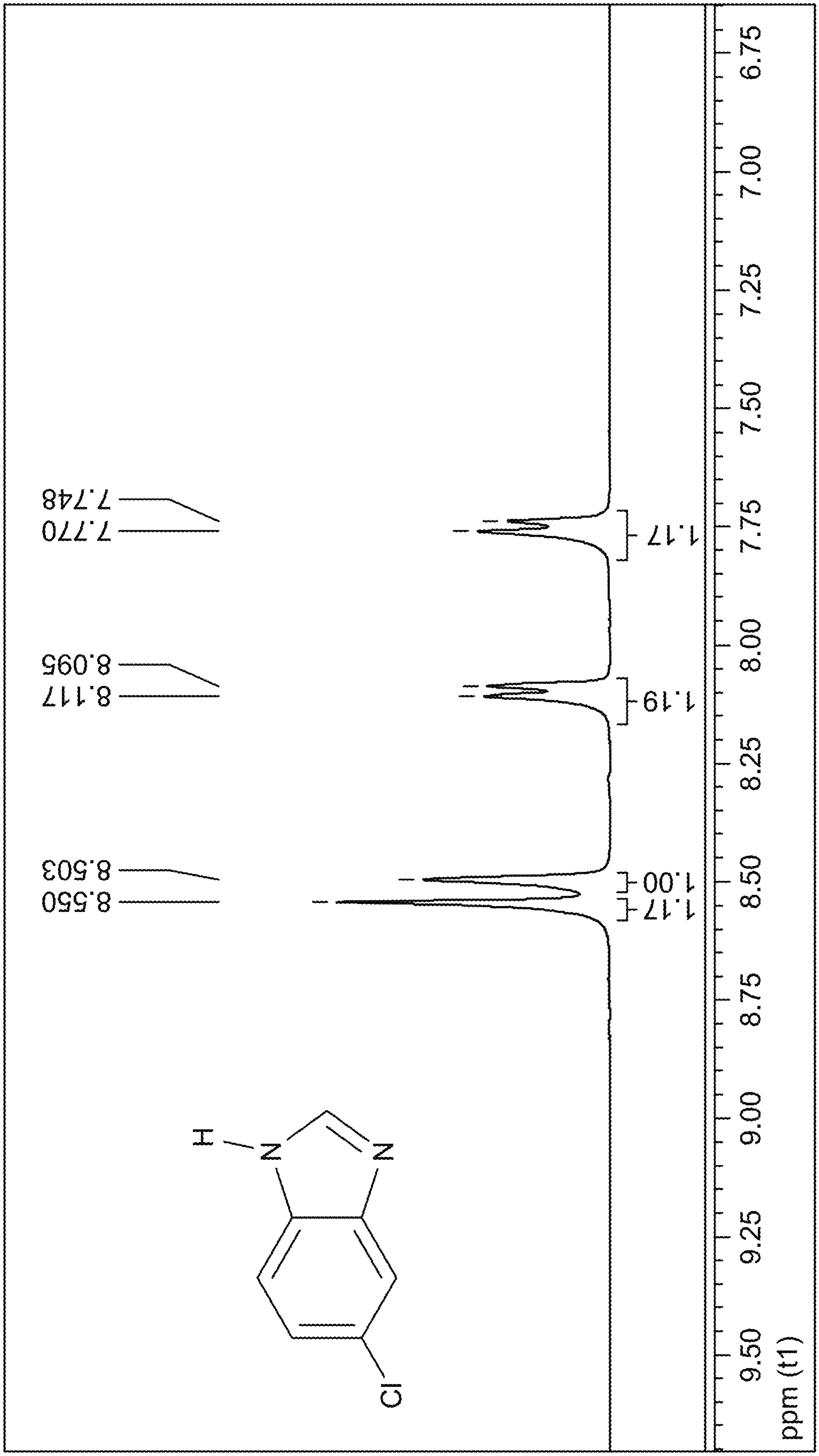
FIG. 18 shows a $^1$H NMR spectrum of 5-chloro-1H-benzo[d]imidazole (entry 2, Table 2), according to certain embodiments.

The $^1H$ and $^{13}C$ NMR of 5-chloro-1H-benzo[d]imidazole (entry 2, Table 5): $^1H$ NMR (DMSO-d6, 400 MHz, ppm.): δ 8.55 (s, 1H), 8.50 (s, 1H), 8.11 (d, J=8.8 Hz, 1H), 7.76 (d, J=8.8 Hz, 1H) (FIG. 18); $^{13}C$ NMR (DMSO-d6, 400 MHz, ppm): δ 146.5, 142.4, 117.3.

Figure 19:
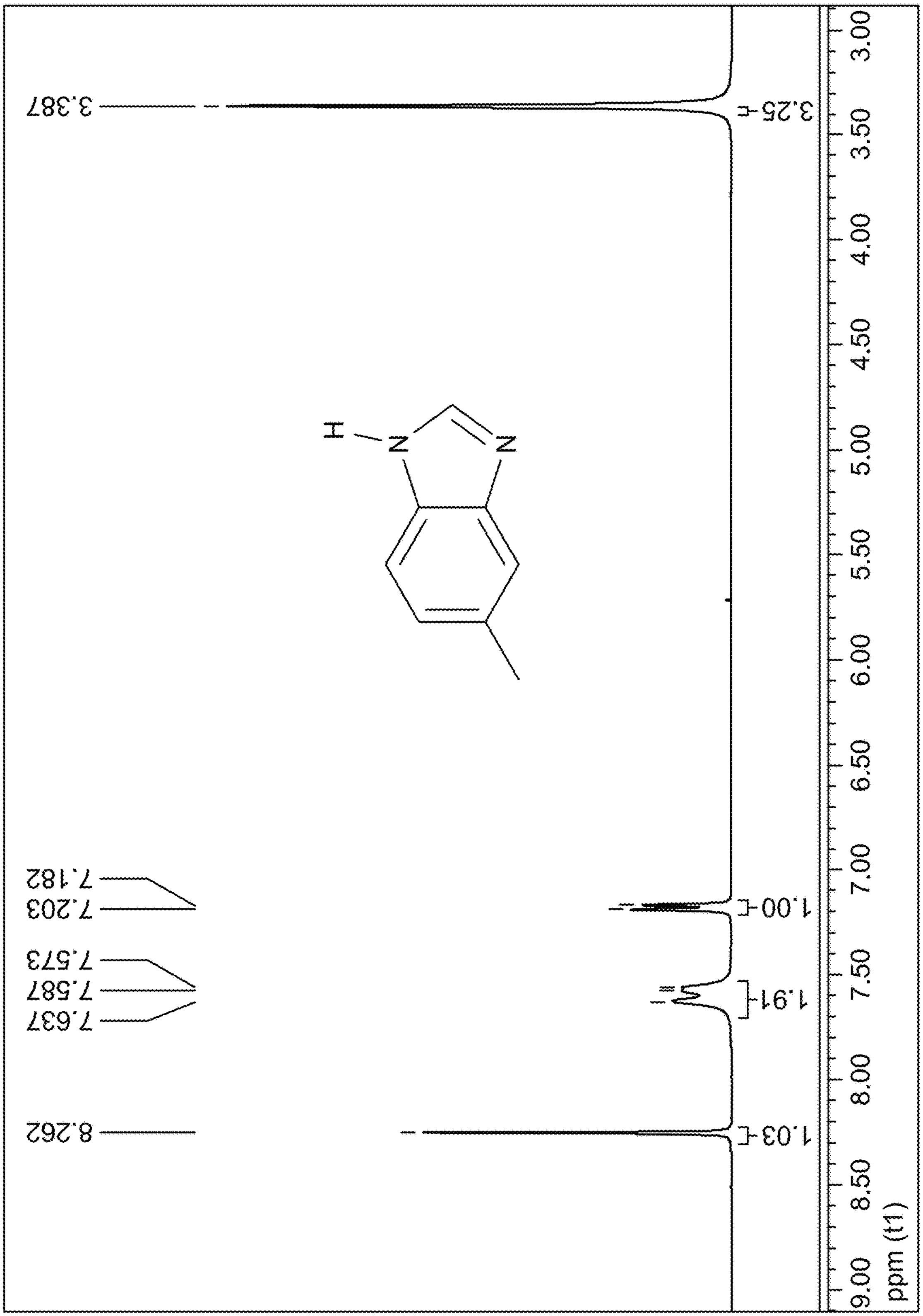
FIG. 19 shows $^1$H NMR spectrum of 5-methyl-1H-benzo[d]imidazole (entry 3, Table 2), according to certain embodiments.

The $^1H$ and $^{13}C$ NMR of 5-methyl-1H-benzo[d]imidazole (entry 3, Table 5): $^1H$ NMR (DMSO-d6, 400 MHz, ppm.): δ 8.26 (s, 1H), 7.64 (s, 1H), 7.57 (d, J=5.6 Hz, 1H), 7.19 (d, J=8.4 Hz, 2H), 3.39 (s, 1H) (FIG. 19); $^{13}C$ NMR (DMSO-d6, 400 MHz, ppm): δ 142.1, 131.3, 123.6, 115.0, 21.7.

Figure 20:
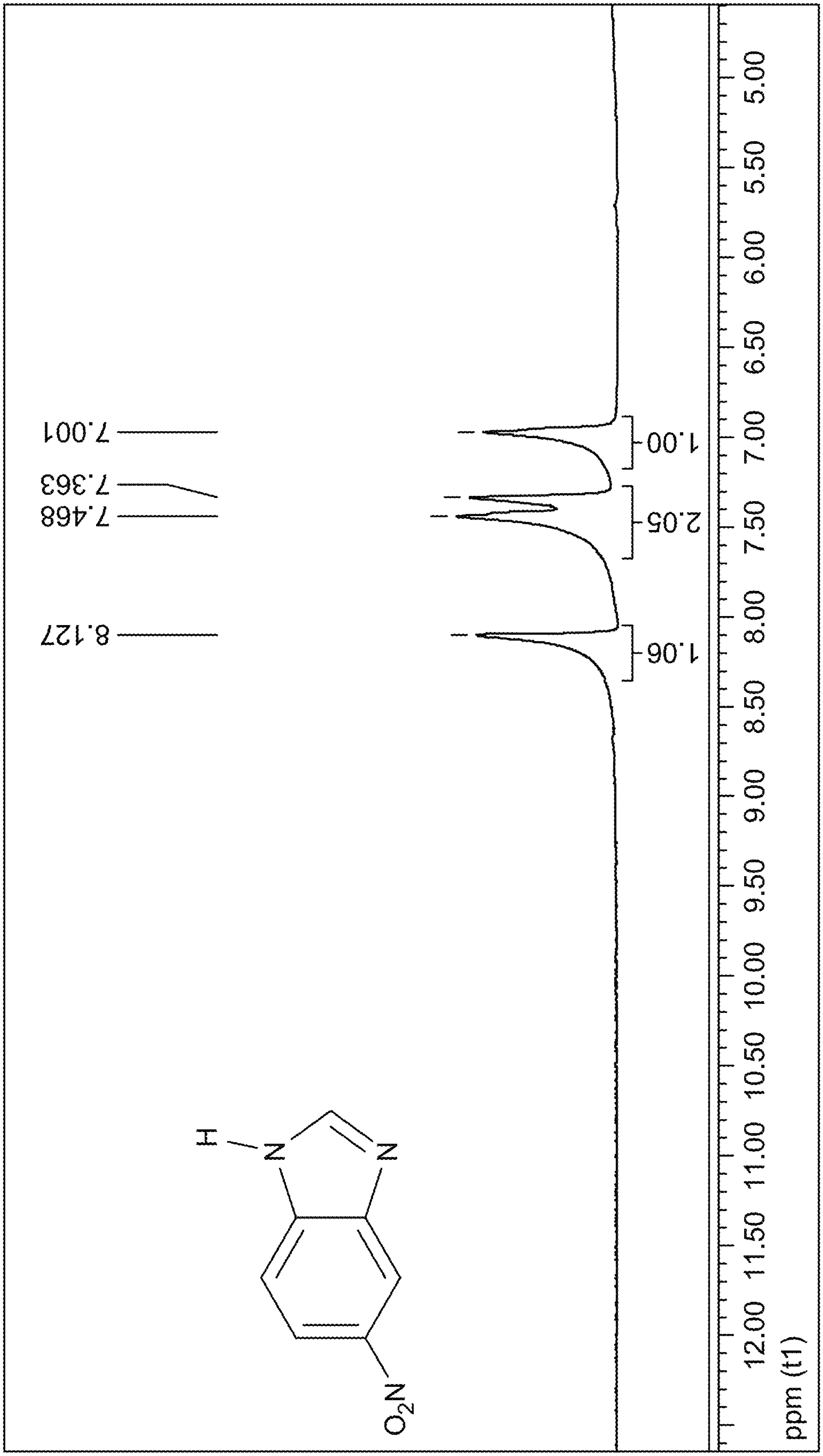
FIG. 20 shows $^1$H NMR spectrum of 5-nitro-1H-benzo[d]imidazole (entry 4, Table 2), according to certain embodiments.

The $^1H$ and $^{13}C$ NMR of 5-nitro-1H-benzo[d]imidazole (entry 4, Table 5): $^1H$ NMR (DMSO-d6, 400 MHz, ppm.): δ 8.13 (s, 1H), 7.47 (s, 1H), 7.36 (s, 1H), 7.00 (s, 1H) (FIG. 20); $^{13}C$ NMR (DMSO-d6, 400 MHz, ppm): δ 143.3, 142.4, 138.7, 118.7, 115.3, 111.9.

TABLE 5

CoNi@C-catalyzed synthesis of various benzimidazoles[a]

| Entry | Substrate | Product | Yield |
|---|---|---|---|
| 1 | 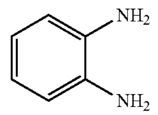 | 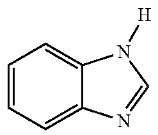 | 81 |
| 2 | 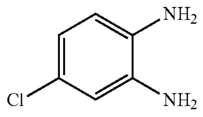 | 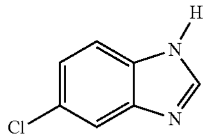 | 78 |
| 3 | 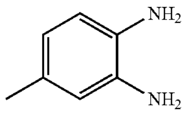 | 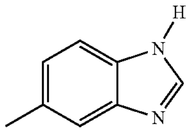 | 82 |
| 4 | 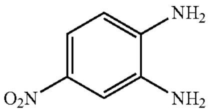 | 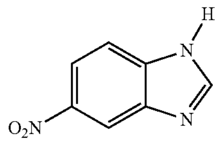 [SMILES: O=[N+]([O-])c1ccc2[nH]cnc2c1] | 80 |

[a]Reaction conditions: substrates, 1.0 mmol; temperature, 115° C.; pressure, 30 bar; time, 18 h.

Figure 21:
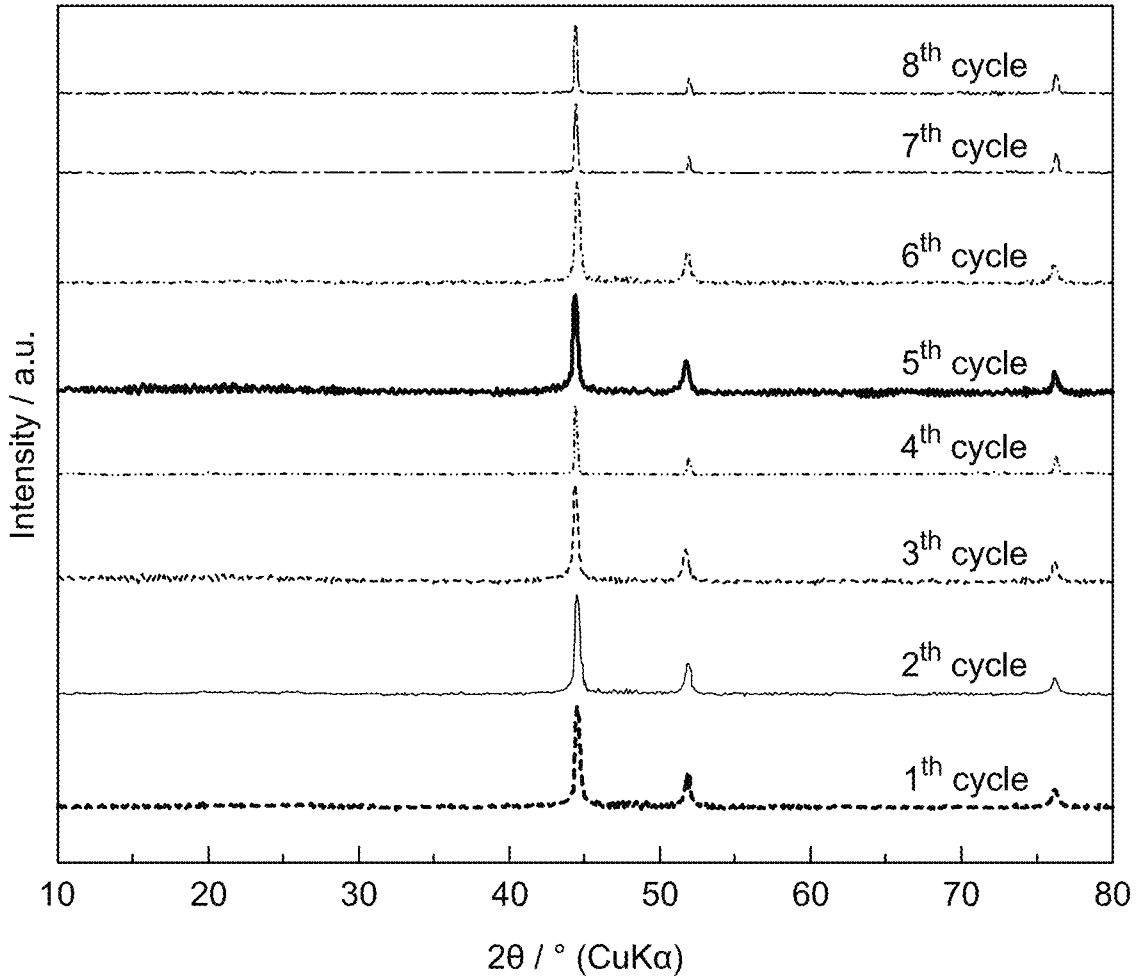
FIG. 21 depicts PXRD of the catalyst CoNi@C after each cycle of catalysis, for 8 cycles, according to certain embodiments.
Figure 22:
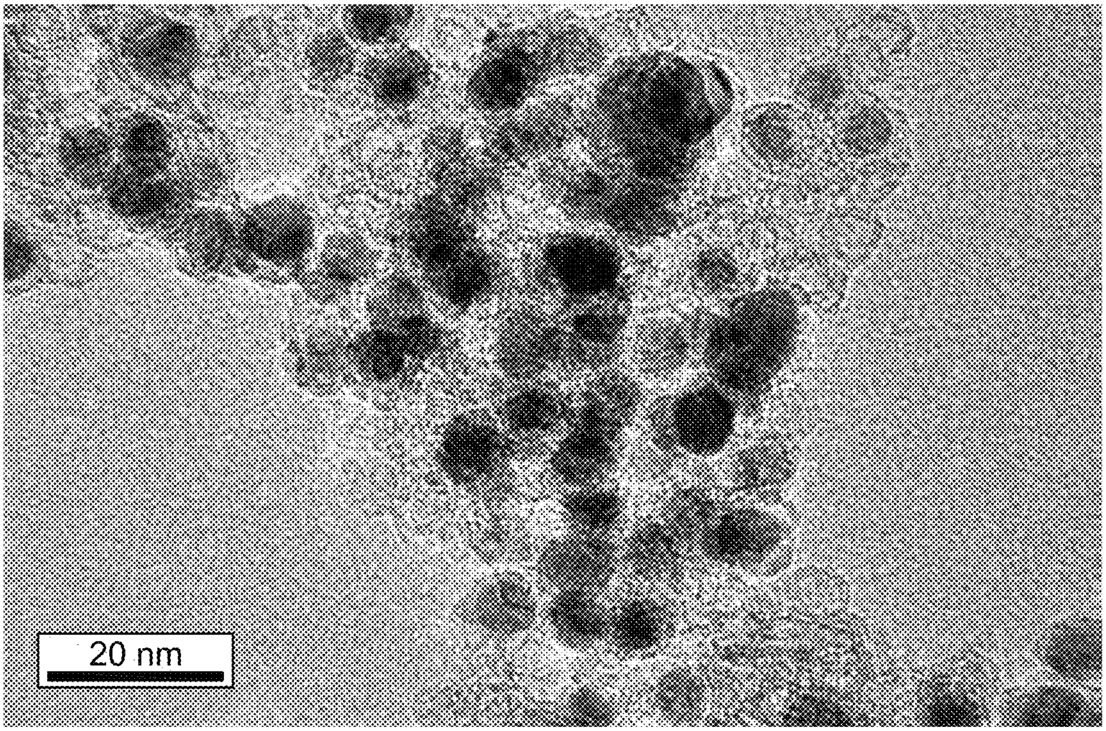
FIG. 22 shows TEM of the catalyst CoNi@C after 8 cycles of catalysis, according to certain embodiments.

The regeneration of the catalyst in the benzimidazole synthesis and discovered that the catalyst could be regenerated up to eight cycles without any loss of crystallinity, as evidenced by the PXRD (FIG. 21) and morphology as seen from the TEM (FIG. 22). A literature review comparing similar types of catalysts used in the synthesis of benzimidazole revealed that the catalyst of the present disclosure had a comparable yield under the corresponding reaction conditions (Table 6).

TABLE 6

Comparative table on reaction yield with the catalyst of the present disclosure and other catalysts disclosed in the literature

| S. No | Catalysts | Condition (temperature/pressure/time) | Yield (%) |
|---|---|---|---|
| 1 | $CH_3COOK$, Phenylsilane | 40° C./1 bar $CO_2$/24 h | 90 |
| 2 | Cu-NPs@COF[a] | 60° C./1 bar $CO_2$/12 h | 95 |
| 3 | $RuCl_2(dppe)_2$ | 120° C./150 bar $CO_2$ + $H_2$/40 h | 92 |
| 4 | Au/$TiO_2$ | 100° C./80 bar $CO_2$ + $H_2$/12 h | 95 |
| 5 | [PS-Zn(II)-SALTETA,[a] | 100° C./1 bar $CO_2$/24 h | 93 |
| 6 | $CoF_2$, $Ph_3P$, CsF | 140° C./60 bar CO2 + $H_2$/24 h | 94 |
| 7 | Cu@U-g-$C_3N_4$[a] | 100° C./25 bar $CO_2$/24 h | 92 |
| 8 | $CuFe_2O_4$ | 180° C./1 bar $CO_2$/12 h | 96 |
| 9 | CoNi@C | 115° C./30 bar $CO_2$ + $H_2$/18 h | 81 |

[a]refers to DMAB—dimethylamine borane.

Example 17: Methanation of $CO_2$

Figure 23:
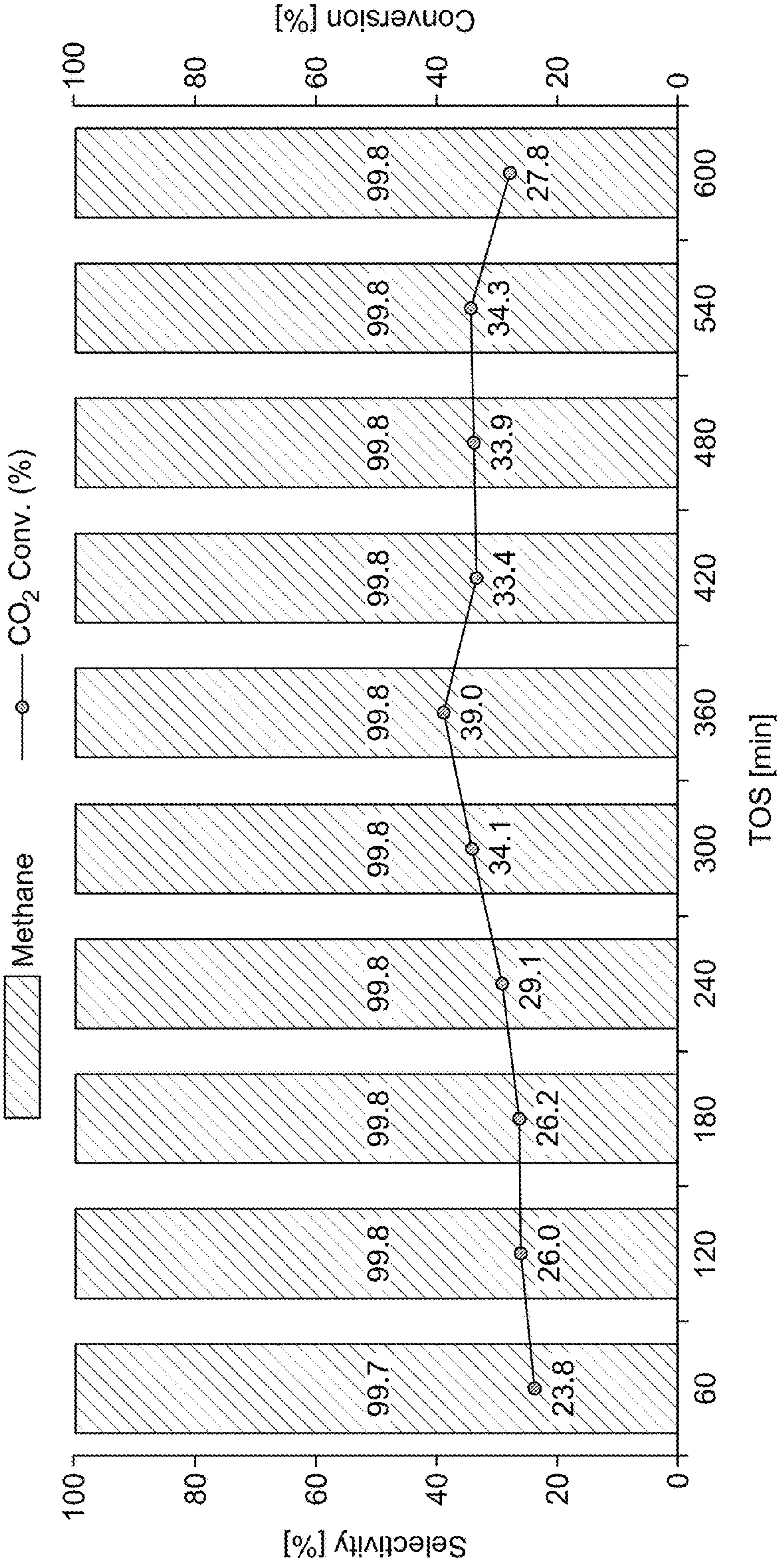
FIG. 23 shows the selectivity and conversion of $CO_2$ to methane with 0.2 g CoNi@C, flow of mixture=15 ml, mixture ($H_2$:$CO_2$)=3:1, at a temperature of 375° C. and 10 bar pressure, at a temperature of 375° C. and 30 bar pressure; according to certain embodiments.

The same catalyst was also explored for the methanation of $CO_2$. The importance of a nickel-based catalyst for the selectivity of methane is well established and known in the art. Supports such as aluminum oxide, titanium oxide, and cerium oxide are commonly employed in the methanation process [Li, Y.; Wang, H.; Jiang, X.; Zhu, J.; Liu, Z.; Guo, X.; Song, C. A short review of recent advances in $CO_2$ hydrogenation to hydrocarbons over heterogeneous catalysts. RSC Adv. 2018, 8, 7651-7669, which is incorporated herein by reference in its entirety]. In the present invention, bimetallic nanoalloy (CoNi@C) of Co and Ni derived from a bimetallic MOF (CoNiBTC) was targeted to determine stability and reactivity for $CO_2$ methanation. The conversion was around 23.8% at the first 1 h of reaction time. The conversion was enhanced to 39.0% after 360 min of reaction time, which shows that the catalyst takes a long time to convert the large volume of reactant in the 27.8% after 600 min of reaction time. Selectivity, on the other hand, was very high toward methane. The selectivity of methane was above 99.7% during the reaction on the stream, which shows that the bimetallic nanoalloy (CoNi@C) of Co and Ni is suitable for the methanation process (FIG. 23).

Figure 24:
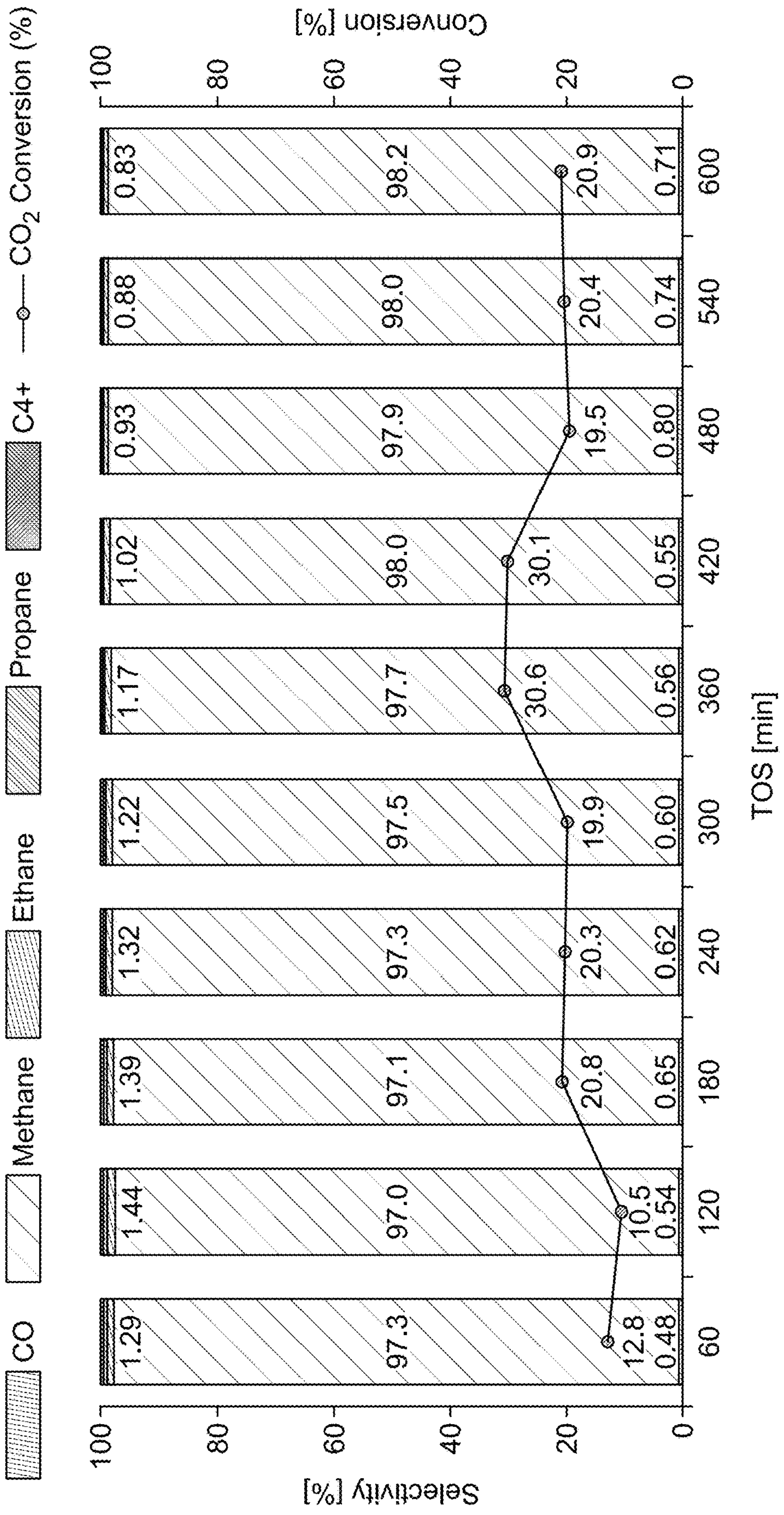
FIG. 24 shows the selectivity and conversion of $CO_2$ to methane with CoNi@C 0.2 g, flow of mixture=15 ml, mixture ($H_2$:$CO_2$)=3:1, at a temperature of 375° C. and 10 bar pressure, according to certain embodiments.
Figure 25:
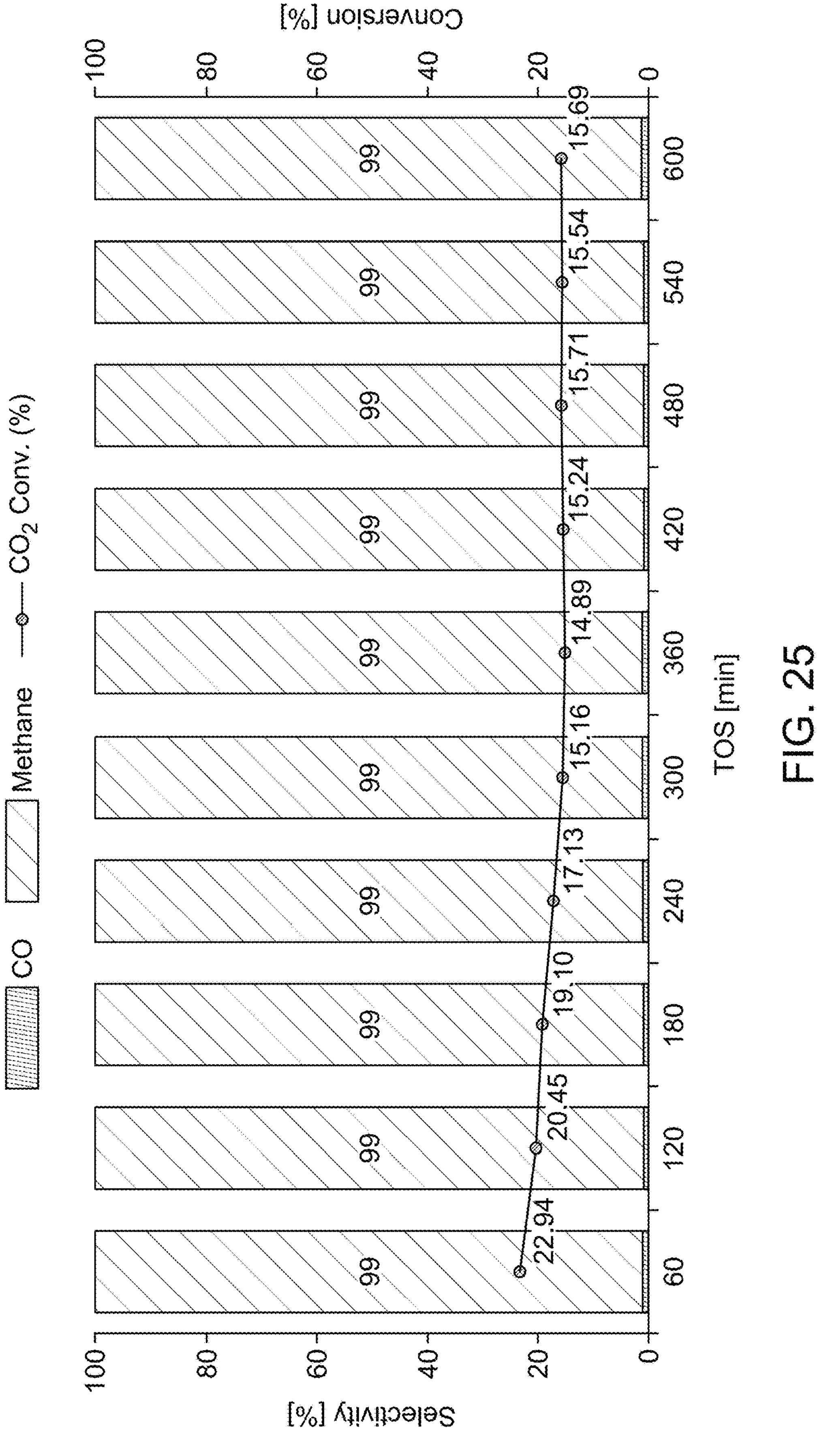
FIG. 25 shows the selectivity and conversion of $CO_2$ to methane with 0.2 g CoNi@C-1, flow of mixture=15 ml, mixture ($H_2$:$CO_2$)=3:1, at a temperature of 375° C. and 10 bar pressure, at a temperature of 375° C. and 30 bar pressure; according to certain embodiments.
Figure 26:
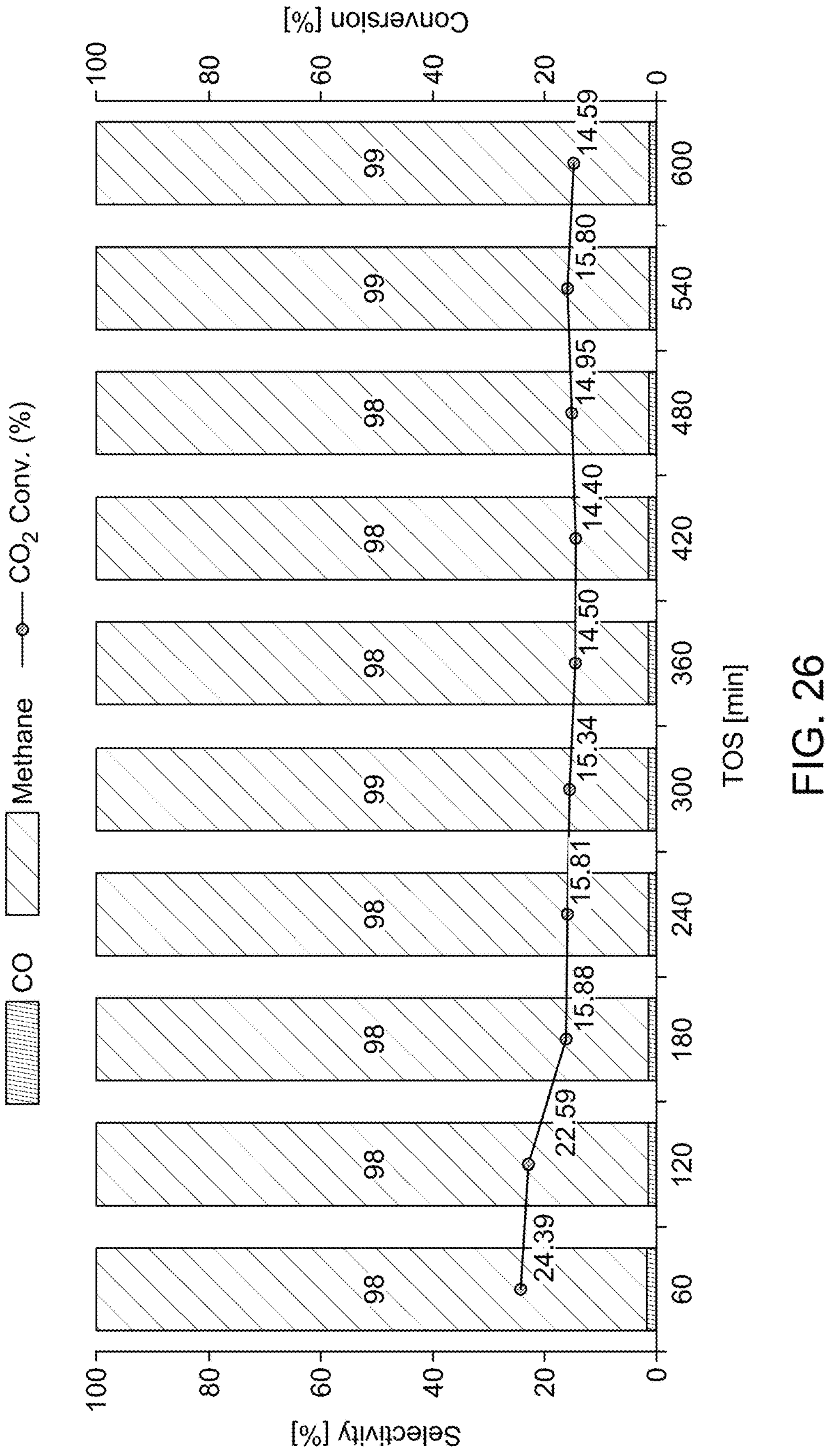
FIG. 26 shows the selectivity and conversion of $CO_2$ to methane with CoNi@C-2 0.2 g, flow of mixture=15 ml, mixture ($H_2$:$CO_2$)=3:1, at a temperature of 375° C. and 10 bar pressure, according to certain embodiments.

In order to comprehend the influence of pressure, similar experiments were conducted at a lower pressure of 10 bar (FIG. 24), which resulted in a reduced 30% yield and 98% selectivity. 5 The influence of the Co/Ni ratio on the methanation reaction was also studied using CoNi@C-1 and CoNi@C-2. It was discovered that when the Co/Ni ratio is 1:1, conversion reduces to 23% while selectivity remains unchanged at 99% (FIG. 25). Alternatively, the same behavior was seen when the Co/Ni ratio was 2:3 (FIG. 26). A comparative study of the selectivity of several catalysts revealed that our catalyst was superior or comparable to others in terms of selectivity (Table 7).

TABLE 7

Comparative table on selectivity with the catalyst of the present disclosure and other catalysts disclosed in the literature.

| S. No | Catalysts | Condition (temperature/pressure/time) | Selectivity (%) |
|---|---|---|---|
| 1 | Ni@C | 350° C. | 98 |
| 2 | Ni/SiO2 | 250° C./1 bar | 98 |
| 3 | Co/SiO2 | 360° C/1 bar | 86.5 |
| 4 | Co/KIT-6 | 360° C. | 94.5 |
| 5 | NiWP | 327° C | 80 |
| 6 | Ni/CeO2-NR | 300° C. | 99 |
| 7 | CoMnxAl2-xO4 | 400° C. | 97 |
| 8 | Ru-TiOx | 259.3° C. | 99.9 |
| 9 | CoNi@C | 375° C./30 bar | 99.8 |

The present invention relates to the method of making the bimetallic nanoalloy composite including at least 20 wt. %, at least 25 wt. %, at least 30 wt. %, at least 35 wt. %, at least 40 wt. %, at least 45 wt. %, at least 50 wt. % of the cobalt nanoparticles and at least 10 wt. %, at least 15 wt. %, at least 20 wt. %, at least 25 wt. %, at least 30 wt. %, of the nickel nanoparticles or mixture thereof. The bimetallic nanoalloy CoNi@C derived from the CoNiBTC MOF acts as a good catalyst for the synthesis of various substituted benzimidazoles from the corresponding o-phenylenediamine in a good yield (78-82%), in the presence of a mixture of $CO_2$ and $H_2$ at elevated temperature and pressure. The same catalyst was also utilized for the 99.7% selective methanation of $CO_2$. The bimetallic BTC MOF as a precursor in the synthesis of functional nanomaterials with a controlled structure and customized compositions, encased in carbon shells with a high dispersion that boosted their catalytic activity.

The method of the present invention include the fixation of $CO_2$ to reduce greenhouse gas emissions. Furthermore, the method of the present invention includes the conversion of atmospheric and industrially produced carbon into methane. In some embodiments, the carbon dioxide is converted into value-added products such as benzimidazole. The method of the present disclosure can be used in the synthesis of pesticides, pharmaceuticals, and materials. According to some embodiments of the present invention, the catalysts produced by the present method are selective in the methanation of $CO_2$.

Numerous modifications and variations of the present disclosure are possible in light of the above teachings. It is therefore to be understood that within the scope of the appended claims, the invention may be practiced otherwise than as specifically described herein.

The invention claimed is:

1. A method of making a bimetallic nanoalloy composite, comprising:

mixing and dissolving a nickel salt, a cobalt salt and an aromatic carboxylic acid in a first solvent to form a first mixture;

mixing acetic acid with the first mixture and heating at a temperature of 150 to 200 degrees Celsius (° C.) form a second mixture;

washing the second mixture with at least one organic solvent and drying to form a bimetallic metal-organic framework (CoNiBTC);

heating the CoNiBTC at a temperature of 600 to 900° C. under a nitrogen stream to form a pyrolyzed composite;

cooling the pyrolyzed composite and exposing to a gas mixture to form the bimetallic nanoalloy composite, wherein the bimetallic nanoalloy composite is in the form of bimetallic nanoalloy composite particles comprising cobalt nanoparticles, nickel nanoparticles and porous carbon layers;

wherein the cobalt nanoparticles present in the bimetallic nanoalloy composite have an average particle size of 5 to 50 nanometers (nm);

wherein the nickel nanoparticles present in the bimetallic nanoalloy composite have an average particle size of 5 to 50 nm; and wherein the nanoparticles of cobalt and nickel are embedded in the porous carbon layers of the bimetallic nanoalloy composite, and are uniformly distributed throughout the bimetallic nanoalloy composite.

2. The method of claim 1, wherein the cobalt nanoparticles are present in the bimetallic nanoalloy composite at a concentration of 20 to 50% by weight based on the total weight of the bimetallic nanoalloy composite.

3. The method of claim 1, wherein the nickel nanoparticles are present in the bimetallic nanoalloy composite at a concentration of 10 to 30% by weight based on the total weight of the bimetallic nanoalloy composite.

4. The method of claim 1, wherein the bimetallic nanoalloy composite is in the form of particles having a surface area of 150 to 210 square meters per gram ($m^2/g$).

5. The method of claim 1, wherein the lattice structure of the bimetallic nanoalloy composite has an average interplanar spacing of 0.05 to 0.5 nm.

6. The method of claim 1, wherein the nickel salt comprises nickel sulfate, nickel acetate, nickel chloride, nickel nitrate, nickel carbonate, nickel phosphate and nickel oxalate, and/or a hydrate thereof.

7. The method of claim 1, wherein the cobalt salt comprises cobalt sulfate, cobalt acetate, cobalt citrate, cobalt iodide, cobalt chloride, cobalt perchlorate, cobalt nitrate, cobalt phosphate, cobalt triflate, cobalt bis(trifluoromethanesulfonyl)imide, cobalt tetrafluoroborate, cobalt bromide, and/or a hydrate thereof.

8. The method of claim 1, wherein the aromatic carboxylic acid comprises at least one of trimesic acid, trimellitic acid, trimellitic anhydride, and pyromellitic acid anhydride.

9. The method of claim 1, wherein the solvent is an amide solvent selected from the group consisting of N-methyl-2-pyrrolidone, N,N-dimethylacetamide, N,N-dimethylformamide, and 1,3-dimethyl-2-imidazolidinone.

10. The method of claim 1, wherein a molar ratio of the nickel salt to the cobalt salt is in a range of 1:10 to 10:1, and wherein a molar ratio of the aromatic carboxylic acid to the combined amount of nickel and cobalt salt in the first mixture is in a range of 1:5 to 5:1.

11. The method of claim 1, wherein the bimetallic metal-organic framework (CoNiBTC) is in the form of particles having a surface area of 650 to 750 $m^2/g$.

12. The method of claim 1, wherein the gas mixture comprises an oxygen gas and a nitrogen gas, and wherein a flow rate ratio of the oxygen gas to the nitrogen gas is in a range of 1:1 to 1:10.

* * * * *